(12) United States Patent
Morriss et al.

(10) Patent No.: US 11,278,402 B2
(45) Date of Patent: Mar. 22, 2022

(54) PROSTHESIS FOR TRANSCATHETER DELIVERY HAVING AN INFOLDING LONGITUDINAL SEGMENT FOR A SMALLER RADIALLY COMPRESSED PROFILE

(71) Applicant: MEDTRONIC, INC., Minneapolis, MN (US)

(72) Inventors: John Morriss, Emerald Hills, CA (US); Joshua Dwork, Santa Rosa, CA (US); Nathaniel Piland, Rohnert Park, CA (US); Finn Rinne, Santa Rosa, CA (US); David Grossman, Santa Rosa, CA (US)

(73) Assignee: MEDTRONIC, INC., Minneapolis, MN (US)

( * ) Notice: Subject to any disclaimer, the term of this patent is extended or adjusted under 35 U.S.C. 154(b) by 11 days.

(21) Appl. No.: 16/794,441

(22) Filed: Feb. 19, 2020

(65) Prior Publication Data
US 2020/0268508 A1    Aug. 27, 2020

Related U.S. Application Data

(60) Provisional application No. 62/808,393, filed on Feb. 21, 2019.

(51) Int. Cl.
*A61F 2/24* (2006.01)
*A61B 17/00* (2006.01)
*A61F 2/07* (2013.01)

(52) U.S. Cl.
CPC .............. *A61F 2/2418* (2013.01); *A61F 2/07* (2013.01); *A61F 2/243* (2013.01)

(58) Field of Classification Search
CPC .. A61F 2/07; A61F 2230/0067; A61F 2/2418; A61F 2/2427; A61F 2/90;
(Continued)

(56) References Cited

U.S. PATENT DOCUMENTS

| | | | |
|---|---|---|---|
| 4,141,364 A | * | 2/1979 | Schultze ............... A61M 16/04 128/207.15 |
| 5,571,175 A | | 11/1996 | Vanney et al. |

(Continued)

FOREIGN PATENT DOCUMENTS

| | | |
|---|---|---|
| EP | 0537487 A1 | 4/1993 |
| WO | 2009094501 A1 | 7/2009 |

(Continued)

OTHER PUBLICATIONS

International Search Report and Written Opinion of the International Searching Authority dated May 20, 2020, International Application No. PCT/US2020/018978.

*Primary Examiner* — Ann Schillinger
(74) *Attorney, Agent, or Firm* — Medler Ferro Woodhouse & Mills PLLC

(57) ABSTRACT

A prosthesis having a radially expanded configuration and a radially compressed configuration includes a frame with a plurality of infolding longitudinal segments. Each of the infolding longitudinal segments of the frame extend an entire length of the frame and is configured to deform radially inward when the prosthesis is in the radially compressed configuration such that a series of longitudinally aligned apices of each infolding longitudinal segment is disposed radially inward of the remainder of the prosthesis. In an embodiment, the frame also includes a plurality of outfolding longitudinal segments. Each of the outfolding longitudinal segments of the frame extend an entire length of the frame and is configured to deform radially outward when the prosthesis is in the radially compressed configuration such that a series of longitudinally aligned apices of each outfolding longitudinal segment is disposed radially outward of the remainder of the prosthesis.

18 Claims, 16 Drawing Sheets

(58) Field of Classification Search
CPC .......... A61F 2/9522; A61F 2/24; A61F 2/962;
A61F 2/2412; A61F 2/958; A61F
2002/075; A61F 2/852; A61F 2/86; A61F
2/243; A61F 2/844
See application file for complete search history.

(56) References Cited

U.S. PATENT DOCUMENTS

| | | | |
|---|---|---|---|
| 7,276,078 | B2 | 10/2007 | Spenser et al. |
| 7,331,991 | B2 | 2/2008 | Kheradvar et al. |
| 7,628,805 | B2 | 12/2009 | Spenser et al. |
| 7,708,775 | B2 | 5/2010 | Rowe et al. |
| 7,780,725 | B2 | 8/2010 | Haug et al. |
| 8,002,825 | B2 | 8/2011 | Letac et al. |
| 8,182,528 | B2 | 5/2012 | Salahieh et al. |
| 8,226,710 | B2 | 7/2012 | Nguyen et al. |
| 8,231,670 | B2 | 7/2012 | Salahieh et al. |
| 8,449,599 | B2 | 5/2013 | Chau et al. |
| 8,603,160 | B2 | 12/2013 | Salahieh et al. |
| 8,623,078 | B2 | 1/2014 | Salahieh et al. |
| 8,628,566 | B2 | 1/2014 | Eberhardt et al. |
| 8,641,757 | B2 | 2/2014 | Pintor et al. |
| 8,668,733 | B2 | 3/2014 | Haug et al. |
| 8,673,000 | B2 | 3/2014 | Tabor et al. |
| 8,734,484 | B2 | 5/2014 | Ahlberg et al. |
| 8,795,357 | B2 | 8/2014 | Yohanan et al. |
| 8,801,706 | B2 | 8/2014 | Rothstein et al. |
| 8,802,356 | B2 | 8/2014 | Braido et al. |
| 9,034,032 | B2 | 5/2015 | McLean et al. |
| 10,016,271 | B2 | 7/2018 | Morriss et al. |
| 10,143,552 | B2 * | 12/2018 | Wallace ................ A61F 2/2418 |
| 10,213,307 | B2 | 2/2019 | Dwork et al. |
| 10,368,990 | B2 * | 8/2019 | Noe ...................... A61M 39/22 |
| 10,492,908 | B2 * | 12/2019 | Hammer ............... A61F 2/2418 |
| 2003/0199963 | A1 | 10/2003 | Tower et al. |
| 2003/0199971 | A1 | 10/2003 | Tower et al. |
| 2004/0030381 | A1 | 2/2004 | Shu |
| 2004/0111111 | A1 | 6/2004 | Lin |
| 2004/0122514 | A1 | 6/2004 | Fogarty et al. |
| 2006/0004442 | A1 | 1/2006 | Spenser et al. |
| 2006/0265056 | A1 | 11/2006 | Nguyen et al. |
| 2007/0239266 | A1 | 10/2007 | Birdsall |
| 2007/0239269 | A1 | 10/2007 | Dolan et al. |
| 2007/0270944 | A1 | 11/2007 | Bergheim et al. |
| 2007/0293944 | A1 | 12/2007 | Spenser et al. |
| 2008/0009940 | A1 | 1/2008 | Cribier |
| 2008/0243245 | A1 | 10/2008 | Thambar et al. |
| 2009/0099653 | A1 | 4/2009 | Suri et al. |
| 2009/0112311 | A1 | 4/2009 | Miles et al. |
| 2009/0192591 | A1 | 7/2009 | Ryan et al. |
| 2010/0036479 | A1 | 2/2010 | Hili et al. |
| 2010/0168844 | A1 | 7/2010 | Toomes et al. |
| 2010/0198238 | A1 | 8/2010 | Sorajja |
| 2010/0277413 | A1 | 11/2010 | Wang et al. |
| 2010/0280589 | A1 | 11/2010 | Styrc |
| 2011/0054466 | A1 | 3/2011 | Rothstein et al. |
| 2011/0098802 | A1 | 4/2011 | Braido et al. |
| 2011/0137397 | A1 | 6/2011 | Chau et al. |
| 2011/0172765 | A1 | 7/2011 | Nguyen et al. |
| 2011/0245911 | A1 | 10/2011 | Quill et al. |
| 2011/0257721 | A1 | 10/2011 | Tabor |
| 2011/0264206 | A1 | 10/2011 | Tabor |
| 2012/0022633 | A1 | 1/2012 | Olson et al. |
| 2012/0035722 | A1 | 2/2012 | Tuval |
| 2012/0041549 | A1 | 2/2012 | Salahieh et al. |
| 2012/0041550 | A1 | 2/2012 | Salahieh et al. |
| 2012/0101572 | A1 | 4/2012 | Kovalsky et al. |
| 2013/0190857 | A1 | 7/2013 | Mitra et al. |
| 2013/0190862 | A1 | 7/2013 | Pintor et al. |
| 2013/0197622 | A1 | 8/2013 | Mitra et al. |
| 2013/0331929 | A1 | 12/2013 | Mitra et al. |
| 2014/0046426 | A1 | 2/2014 | Kovalsky |
| 2014/0114402 | A1 | 4/2014 | Ahlberg et al. |
| 2014/0114406 | A1 | 4/2014 | Salahieh et al. |
| 2014/0188219 | A1 | 7/2014 | Conklin et al. |
| 2014/0194975 | A1 | 7/2014 | Quill et al. |
| 2014/0194981 | A1 | 7/2014 | Menk et al. |
| 2014/0222135 | A1 | 8/2014 | Forster et al. |
| 2014/0222144 | A1 | 8/2014 | Eberhardt et al. |
| 2014/0236287 | A1 | 8/2014 | Clague et al. |
| 2014/0243966 | A1 | 8/2014 | Garde et al. |
| 2014/0243969 | A1 | 8/2014 | Venkatasubramanian et al. |
| 2014/0257475 | A1 | 9/2014 | Gross et al. |
| 2014/0277388 | A1 | 9/2014 | Skemp |
| 2014/0277417 | A1 | 9/2014 | Schraut et al. |
| 2014/0277419 | A1 | 9/2014 | Garde et al. |
| 2014/0277423 | A1 | 9/2014 | Alkhatib et al. |
| 2014/0277424 | A1 | 9/2014 | Oslund |
| 2014/0277425 | A1 | 9/2014 | Dakin |
| 2014/0277426 | A1 | 9/2014 | Dakin et al. |
| 2014/0277428 | A1 | 9/2014 | Skemp et al. |
| 2015/0148886 | A1 | 5/2015 | Rao et al. |
| 2016/0120644 | A1 | 5/2016 | Rowe |
| 2016/0310267 | A1 * | 10/2016 | Zeng ..................... A61F 2/2409 |
| 2016/0310268 | A1 * | 10/2016 | Oba ...................... A61F 2/2436 |
| 2018/0055629 | A1 | 3/2018 | Oba et al. |

FOREIGN PATENT DOCUMENTS

| | | |
|---|---|---|
| WO | 2011051043 A1 | 5/2011 |
| WO | 2012032187 A1 | 3/2012 |
| WO | 2013033791 A1 | 3/2013 |
| WO | 2014072439 A1 | 5/2014 |

* cited by examiner

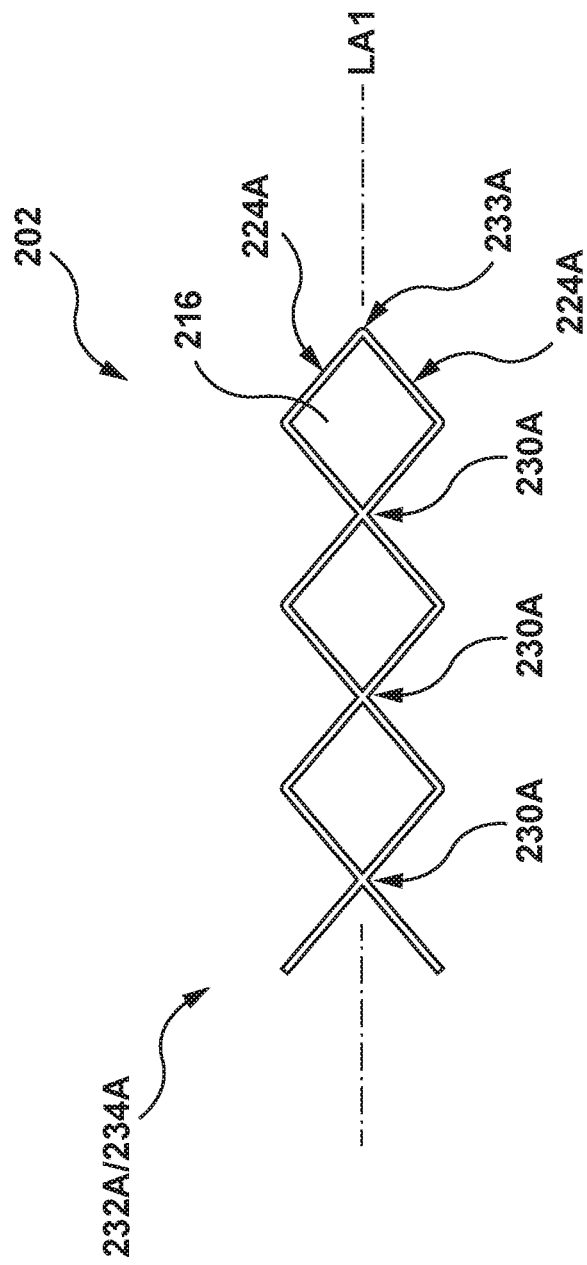

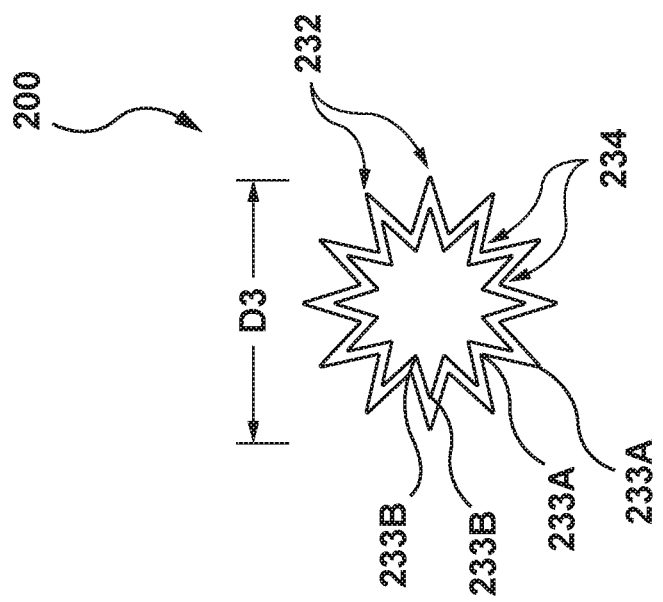
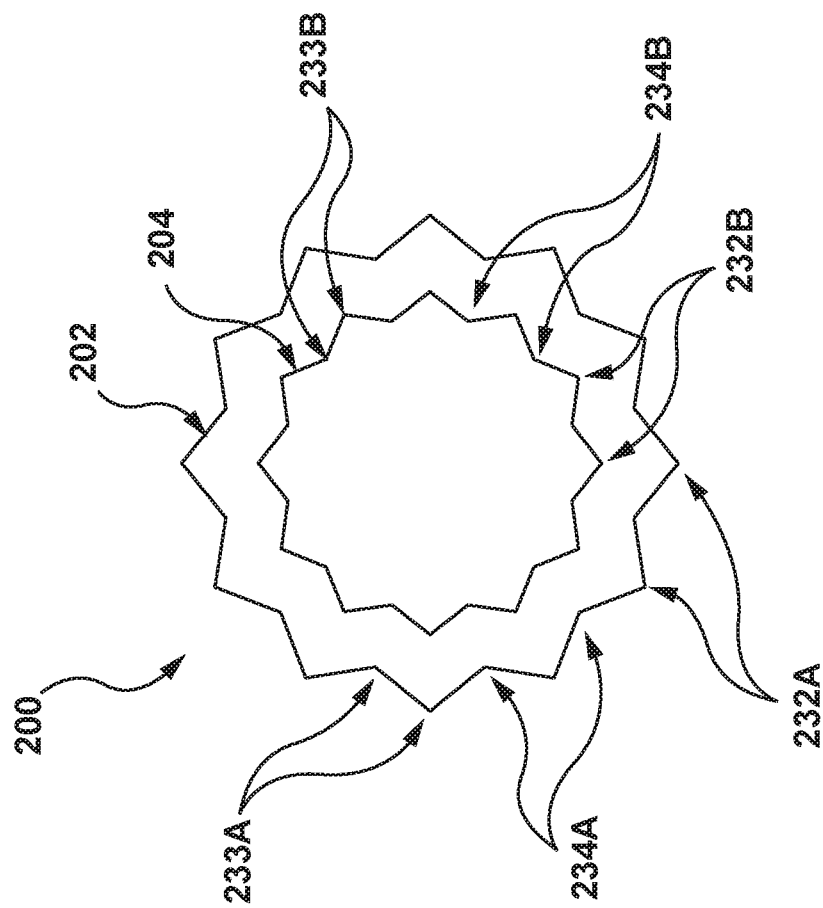

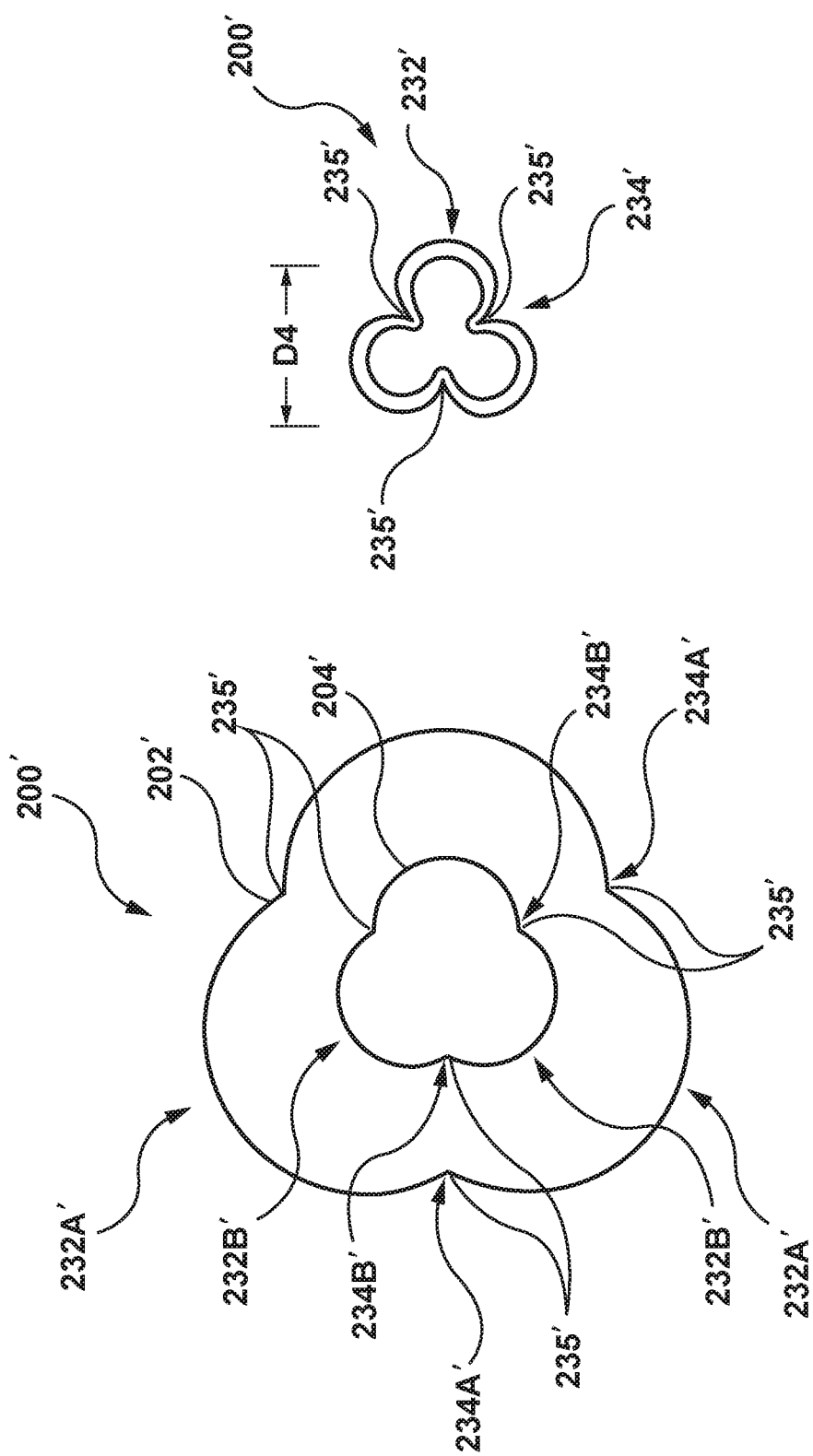

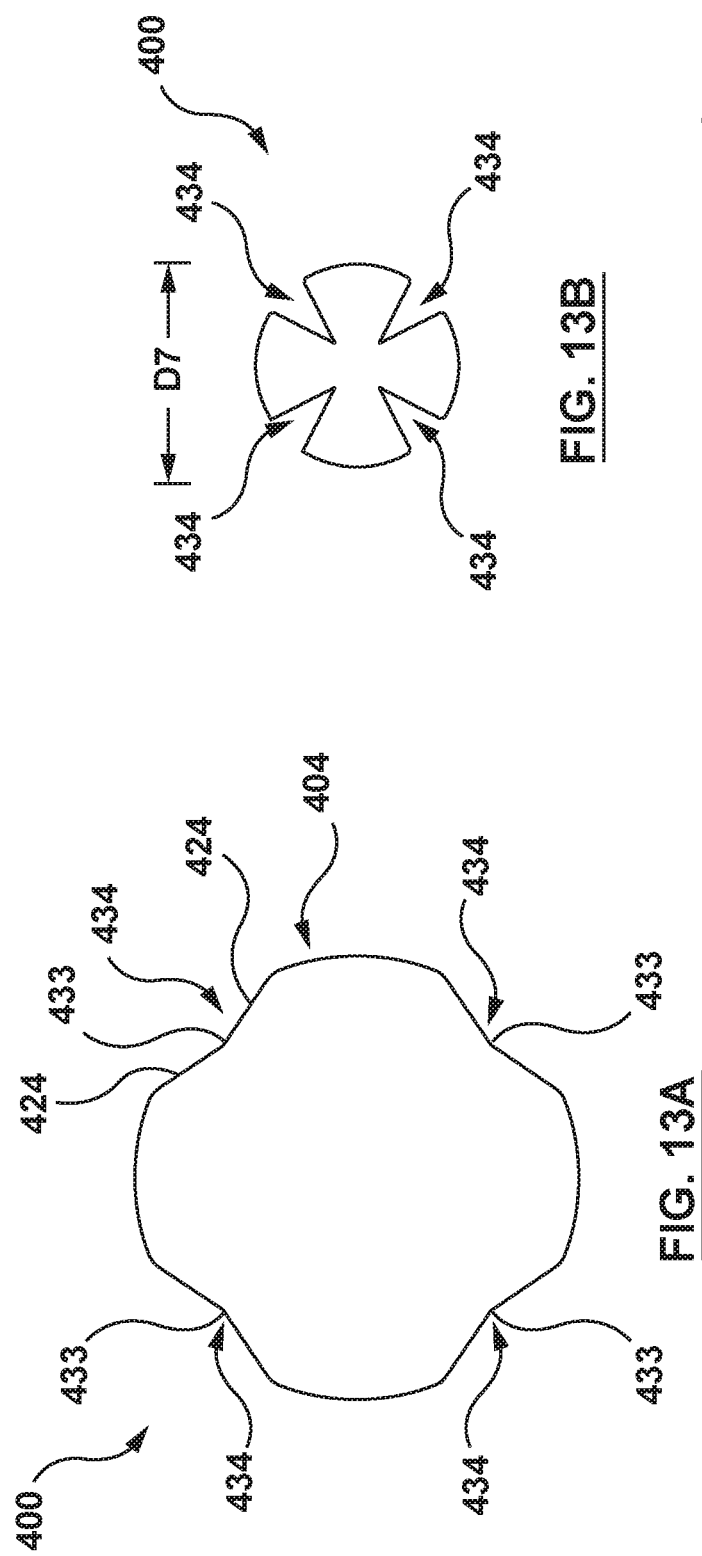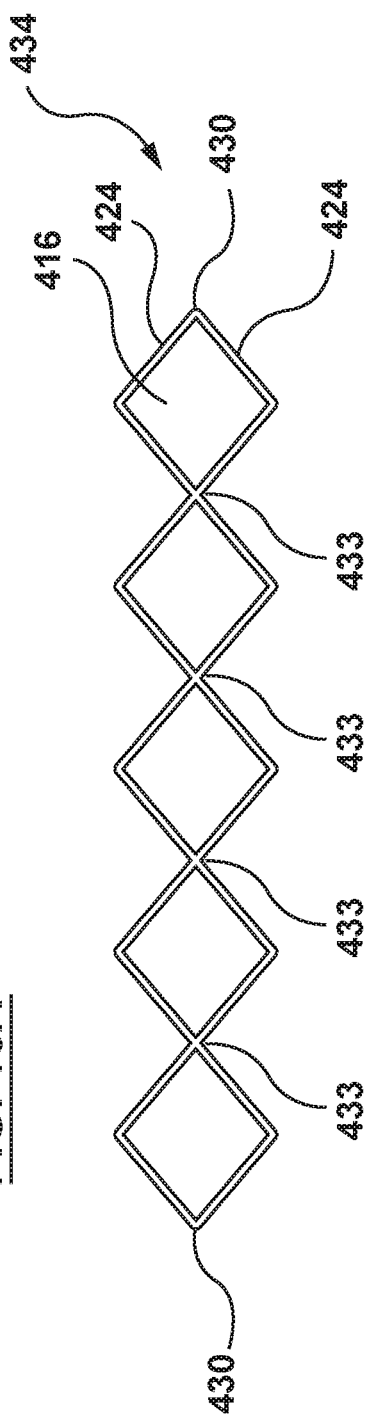

PROSTHESIS FOR TRANSCATHETER DELIVERY HAVING AN INFOLDING LONGITUDINAL SEGMENT FOR A SMALLER RADIALLY COMPRESSED PROFILE

CROSS-REFERENCE TO RELATED APPLICATIONS

This application claims the benefit of U.S. Provisional Patent Application Ser. No. 62/808,393, filed Feb. 21, 2019, which is hereby incorporated by reference in its entirety for all purposes.

FIELD OF THE INVENTION

The present invention relates to prostheses for transcatheter delivery. More particularly, the present invention relates to a prosthesis that compresses to smaller radially compressed profiles for transcatheter delivery.

BACKGROUND OF THE INVENTION

The human heart is a four chambered, muscular organ that provides blood circulation through the body during a cardiac cycle. The four main chambers include the right atrium and right ventricle which supplies the pulmonary circulation, and the left atrium and left ventricle which supplies oxygenated blood received from the lungs to the remaining body. To ensure that blood flows in one direction through the heart, atrioventricular valves (tricuspid and mitral valves) are present between the junctions of the atrium and the ventricles, and semi-lunar valves (pulmonary valve and aortic valve) govern the exits of the ventricles leading to the lungs and the rest of the body. These valves contain leaflets or cusps that open and shut in response to blood pressure changes caused by the contraction and relaxation of the heart chambers. The leaflets move apart from each other to open and allow blood to flow downstream of the valve, and coapt to close and prevent backflow or regurgitation in an upstream manner.

Diseases associated with heart valves, such as those caused by damage or a defect, can include stenosis and valvular insufficiency or regurgitation. For example, valvular stenosis causes the valve to become narrowed and hardened which can prevent blood flow to a downstream heart chamber from occurring at the proper flow rate and may cause the heart to work harder to pump the blood through the diseased valve. Valvular insufficiency or regurgitation occurs when the valve does not close completely, allowing blood to flow backwards, thereby causing the heart to be less efficient. A diseased or damaged valve, which can be congenital, age-related, drug-induced, or in some instances, caused by infection, can result in an enlarged, thickened heart that loses elasticity and efficiency. Some symptoms of heart valve diseases can include weakness, shortness of breath, dizziness, fainting, palpitations, anemia and edema, and blood clots which can increase the likelihood of stroke or pulmonary embolism. Symptoms can often be severe enough to be debilitating and/or life threatening.

Heart valve prostheses have been developed for repair and replacement of diseased and/or damaged heart valves. Such heart valve prostheses can be percutaneously delivered and deployed at the site of the diseased heart valve through catheter-based delivery systems. Such heart valve prostheses can be delivered while in a radially compressed configuration so that the valve prosthesis can be advanced through the patient's vasculature. Once positioned at the treatment site, the valve prosthesis can be expanded to engage tissue at the diseased heart valve region to, for instance, hold the valve prosthesis in position. While these valve prostheses offer minimally invasive methods for heart valve repair and/or replacement, challenges remain to providing effective, less invasive, smaller crossing profile prosthetic delivery systems. Recent heart valve prosthesis designs have incorporated additional graft material to aid in sealing to prevent paravalvular leakage (PVL). However, this additional material adds to the crossing profile of the heart valve prosthesis. The increased crossing profile, especially for radial interventions and inter-atrial septum puncture, limits the size of the heart valve prosthesis and/or the feasibility of transcatheter delivery.

In an example, as a heart valve prosthesis is compressed/loaded for delivery, portions of the frame of the heart valve prosthesis are pushed closer and closer together to obtain the desired crossing profile. On occasion, during loading, the heart valve prosthesis is compressed to the point where the frame can no longer find space along the desired circumference of the heart valve prosthesis and portions of the frame of the heart valve prosthesis will buckle, fold, or otherwise deform radially inward. When the heart valve prosthesis deforms radially inward as described above, the frame is exposed to increased stresses that may damage the frame and negatively affect the structural integrity of the heart valve prosthesis.

Accordingly, there is a need for heart valve prostheses that more efficiently compress to smaller profiles without damaging the frame of the heart valve prosthesis.

BRIEF SUMMARY OF THE INVENTION

Embodiments hereof are directed to a prosthesis having a radially expanded configuration and a radially compressed configuration. The prosthesis includes a frame. The frame includes an infolding longitudinal segment that extends an entire length of the frame and is configured to fold radially inward when the prosthesis is in the radially compressed configuration such that a series of longitudinally aligned apices of the infolding longitudinal segment is disposed radially inward of the remainder of the prosthesis.

In an embodiment hereof, the prosthesis is a heart valve prosthesis. The heart valve prosthesis includes a valve frame, and a prosthetic valve component coupled to the valve frame. In some embodiments, the heart valve prosthesis can also include an anchoring frame surrounding and coupled to the valve frame and/or a graft material coupled to at least one of the valve frame and the anchoring frame. The valve frame includes an infolding longitudinal segment that extends an entire length of the valve frame and is configured to fold radially inward when the prosthesis is in the radially compressed configuration such that a series of longitudinally aligned apices of the infolding longitudinal segment is disposed radially inward of the remainder of the prosthesis. Embodiments that include an anchoring frame, the anchoring frame includes an infolding longitudinal segment that extends an entire length of the anchoring frame and is configured to fold radially inward when the prosthesis is in the radially compressed configuration such that a series of longitudinally aligned apices of the infolding longitudinal segment is disposed radially inward of the remainder of the prosthesis. The infolding longitudinal segment of the anchoring frame is radially aligned with the infolding longitudinal segment of the valve frame.

In another embodiment hereof, the prosthesis includes a frame having a plurality of infolding longitudinal segments and a plurality of outfolding longitudinal segments. Each of the infolding longitudinal segments of the frame extend an entire length of the frame and is configured to deform radially inward when the prosthesis is in the radially compressed configuration such that a series of longitudinally aligned apices of each infolding longitudinal segment is disposed radially inward of the remainder of the prosthesis. Each of the outfolding longitudinal segments of the frame extend an entire length of the frame and is configured to deform radially outward when the prosthesis is in the radially compressed configuration such that a series of longitudinally aligned apices of each outfolding longitudinal segment is disposed radially outward of the remainder of the prosthesis.

BRIEF DESCRIPTION OF DRAWINGS

The foregoing and other features and advantages of the invention will be apparent from the following description of embodiments thereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 5B depicts a side view of a longitudinal segment of an anchoring frame of the heart valve prosthesis of FIG. 4.

FIG. 6A depicts a cross-sectional view of the heart valve prosthesis of FIG. 4, wherein the heart valve prosthesis is in the radially expanded configuration.

FIG. 6B depicts a cross-sectional view of the heart valve prosthesis of FIG. 4, wherein the heart valve prosthesis is in a radially compressed configuration.

FIG. 8A depicts a cross-sectional view of a heart valve prosthesis with a focal area configuration of longitudinal segments thereof in accordance with an embodiment hereof, wherein the heart valve prosthesis is in a radially expanded configuration.

FIG. 8B depicts cross-sectional view of the heart valve prosthesis of FIG. 8A, wherein the heart valve prosthesis is in a radially compressed configuration.

FIG. 13A depicts a cross-sectional view of a heart valve prosthesis with a plurality of infolding longitudinal segments thereof in accordance with an embodiment hereof, wherein the heart valve prosthesis is in a radially expanded configuration.

FIG. 13B depicts a cross-sectional view of the heart valve prosthesis of FIG. 13A, wherein the heart valve prosthesis is in a radially compressed configuration.

FIG. 13C depicts a side view of a longitudinal segment of a frame of the heart valve prosthesis of FIG. 13A.

DETAILED DESCRIPTION OF THE INVENTION

Specific embodiments of the present invention are now described with reference to the figures, wherein like reference numbers indicate identical or functionally similar elements. The terms "distal" and "proximal", when used in the following description to refer to a native vessel, native valve, or a device to be implanted into a native vessel or native valve, such as a heart valve prosthesis, are with reference to the direction of blood flow. Thus, "distal" and "distally" refer to positions in a downstream direction with respect to the direction of blood flow and the terms "proximal" and "proximally" refer to positions in an upstream direction with respect to the direction of blood flow.

The following detailed description is merely exemplary in nature and is not intended to limit the invention or the application and uses of the invention. Although the description of embodiments hereof is in the context of the treatment of blood vessels such as the aorta, and heart valves such as the pulmonary, aortic, mitral, or tricuspid valve, the invention may also be used in any other body passageways where it is deemed useful. Furthermore, there is no intention to be bound by any expressed or implied theory presented in the preceding technical field, background, brief summary or the following detailed description.

Figure 1A:
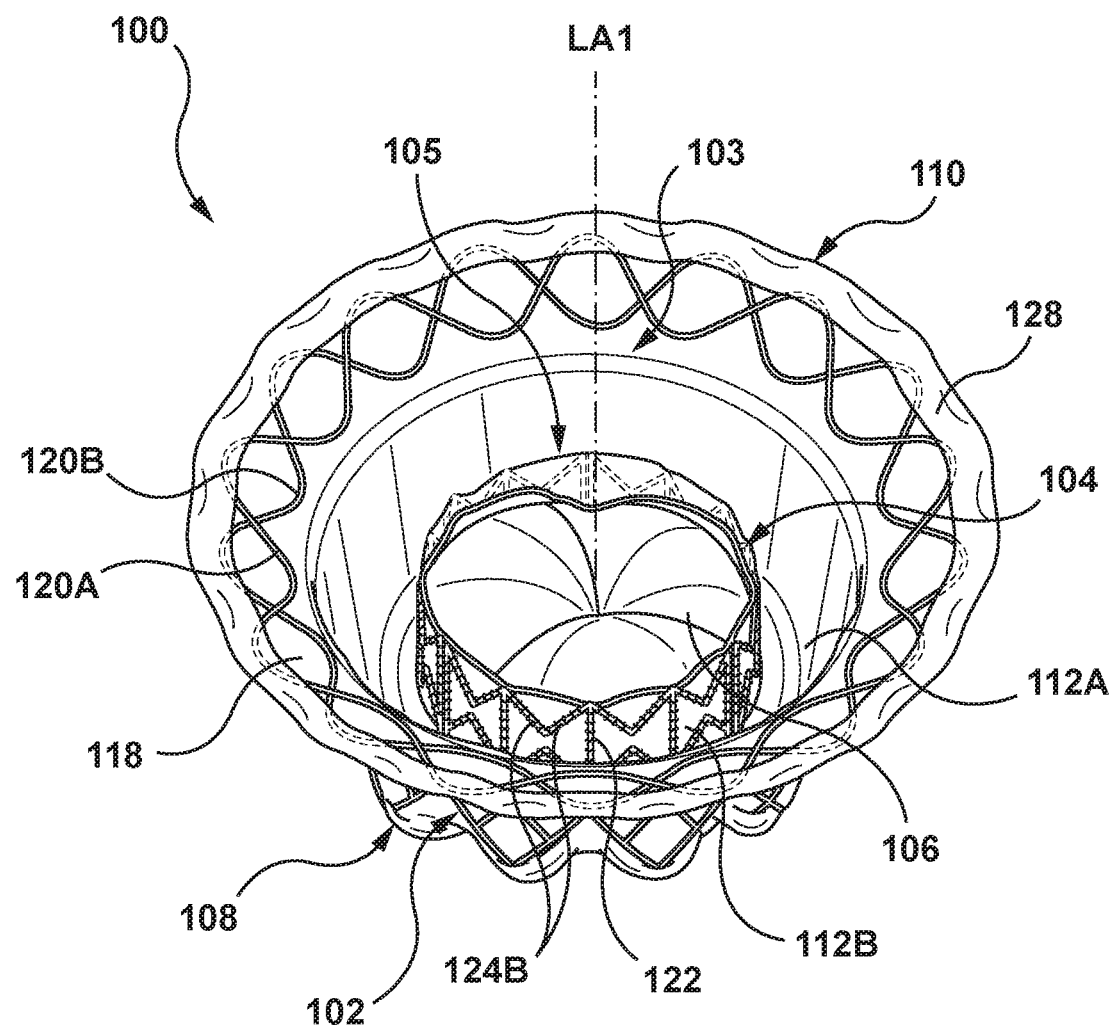
FIG. 1A depicts a perspective view of an exemplary heart valve prosthesis for use in embodiments hereof, wherein the heart valve prosthesis is in a radially expanded configuration.
Figure 1C:
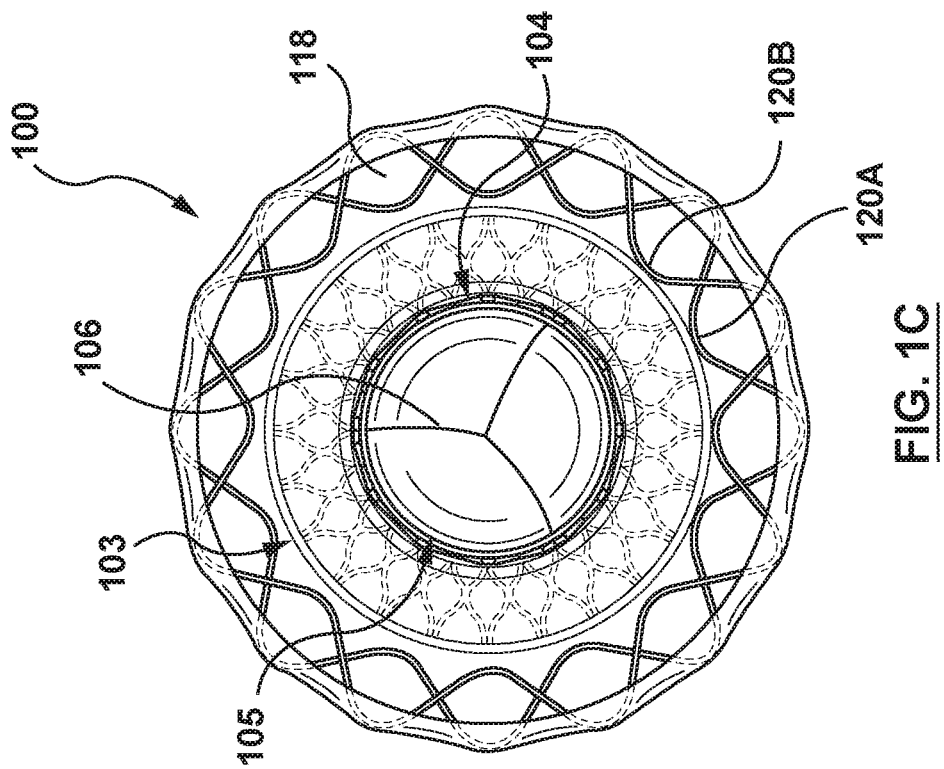
FIG. 1C depicts a top view of the heart valve prosthesis of FIG. 1A, wherein the heart valve prosthesis is in the radially expanded configuration.
Figure 1B:
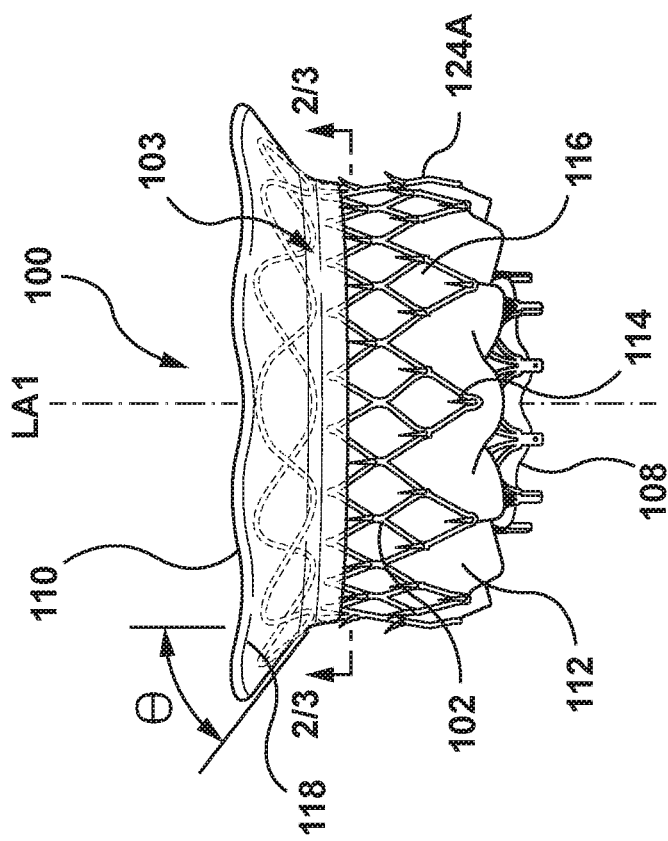
FIG. 1B depicts a side view of the heart valve prosthesis of FIG. 1A, wherein the heart valve prosthesis is in the radially expanded configuration.

FIGS. 1A, 1B, and 1C are perspective, side, and top views, respectively, of an exemplary heart valve prosthesis 100 for use in embodiments hereof, wherein the heart valve prosthesis 100 is in a radially expanded configuration. The heart valve prosthesis 100 is illustrated herein in order to facilitate description of the present invention. It is understood that any number of alternate heart valve prostheses and/or stent assemblies can be used with the invention described herein. The heart valve prosthesis 100 is merely exemplary and is similar to heart valve prostheses described in more detail in U.S. Pat. No. 9,034,032 to McLean et al. and International Patent Application No. PCT/US2014/029549 to McLean et al, each of which is herein incorporated by reference in its entirety. Other non-limiting examples of transcatheter heart valve prostheses that can be used with the invention described herein are described in U.S. Patent Application Publication No. 2012/0101572 to Kovalsky et al., U.S. Patent Application Publication No. 2012/0035722 to Tuval, U.S. Patent Application Publication No. 2006/0265056 to Nguyen et al., U.S. Patent Application Publication No. 2007/05409266 to Birdsall, and U.S. Patent Application Publication No. 2007/05409269 to Dolan et al., each of which is incorporated by reference herein in its entirety.

As shown in FIGS. 1A-1C, the heart valve prosthesis 100 includes an anchoring frame 102 at least partially surrounding and coupled to a valve frame 104. The heart valve prosthesis 100 further includes a prosthetic valve 106 coupled to, mounted within, or otherwise carried by the valve frame 104. The heart valve prosthesis 100 is configured for placement within a native mitral valve and includes a downstream or distal end portion, referred to herein as an outflow portion 108, and an upstream or proximal end portion, referred to herein as an inflow portion 110. The heart valve prosthesis 100 also includes tissue engaging elements 114 (which are best shown on FIG. 1B). For example, the tissue engaging elements 114 may be spikes or barbs disposed on an outer wall or surface of the anchoring frame 102 and extending in an upward and/or radially outward direction to engage, and in some embodiments, penetrate the native tissue to facilitate retention or maintain position of the device in a desired implanted location.

The anchoring frame 102 is a generally tubular component or stent. In the embodiment shown in FIGS. 1A-1C, the anchoring frame 102 has a funnel-like or hyperboloid shape or profile. Further, as best shown on FIG. 1B, the anchoring frame 102 includes diamond-shaped openings 116 that may be formed by a laser-cut manufacturing method and/or another conventional frame forming methods. For example, the anchoring frame 102 may be laser cut from a single metal tube into the desired geometry, creating a tubular scaffold of interconnected struts 124A that form the diamond-shaped openings 116. The anchoring frame 102 may then be shaped into a desired configuration, e.g. funnel-like or hyperboloid shape, using known shape-setting techniques for such materials. It will be understood the anchoring frame 102 may have other shapes and configurations. For example, in another embodiment, the anchoring frame 102 may include a plurality of posts connected circumferentially by a plurality of struts as described herein with respect to the valve frame 104.

The heart valve prosthesis 100 further includes a brim 118. The brim 118 is disposed at the inflow portion 110 of the heart valve prosthesis 100 and is attached to and extends from an inflow end 103 of the anchoring frame 102. The brim 118 is a flared lip or ridge of the anchoring frame 102 that extends at least partially radially outward relative to the anchoring frame 102. As formed and as best shown in the side view of FIG. 1B, the brim 118 may be disposed at an angle Θ relative to the outer wall or surface of the anchoring frame 102. For example, the angle Θ may be between 30 and 90 degrees. In an embodiment, the angle Θ may be between 40 and 50 degrees. In the embodiment shown in FIGS. 1A-1C, the brim 118 includes two sinusoidal rings 120A, 120B and a sealing component 128 disposed over or covering at least a downstream surface of the sinusoidal rings 120A, 120B. The sinusoidal rings 120A, 120B are disposed out of phase relative to each other, and may be woven together or may be disposed in an overlapping manner and coupled together. The sealing component 128 is formed from a suitable natural or biological material such as pericardium or another membranous tissue including, but not limited to intestinal submucosa. Alternatively, the sealing component 128 may be a low-porosity woven fabric, such as polyester, polyethylene terephthalate (PET), or polytetrafluoroethylene (PTFE), or may be a knit or woven polyester, such as a polyester or PTFE knit.

The valve frame 104 is a generally tubular component or stent that supports the prosthetic valve 106 within the interior of the valve frame 104. In some embodiments, the valve frame 104 includes a plurality of posts 122 connected circumferentially by a plurality of struts 124B. The plurality of posts 122 and the plurality of struts 124B may be arranged in a variety of geometrical patterns that expand and provide sufficient resilience and column strength for maintaining the integrity of the prosthetic valve 106. Generally, the plurality of posts 122 extend along an axial direction generally parallel to the longitudinal axis LA1 of the heart valve prosthesis 100. Further, the plurality of posts 122 extend axially or longitudinally across multiple rows of the plurality of struts 124B to provide column strength to the valve frame 104. The plurality of struts 124B extend circumferentially around and transverse to the longitudinal axis LA1. As will be understood, the valve frame 104 may have other shapes and configurations. For example, in another embodiment, the valve frame 104 may be laser cut from a single metal tube into the desired geometry, creating a tubular scaffold of interconnected struts.

In embodiments hereof, both the anchoring frame 102 and the valve frame 104 are self-expanding to return to a radially expanded state from a radially compressed state and may be made from materials such as, but not limited to stainless steel, a pseudo-elastic metal such as a nickel titanium alloy (e.g. NITINOL), or a so-called super alloy, which may have a base metal of nickel, cobalt, chromium, or other metal. "Self-expanding" as used herein means that a structure/component has a mechanical memory to return to the radially expanded configuration or state as described herein. Alternatively, the heart valve prosthesis 100 may be balloon-expandable or mechanically expandable. Whether the valve frame 104 is self-expanding, balloon-expandable, or mechanically expandable, the heart valve prosthesis 100 has a radially compressed configuration for delivery within a delivery system and the radially expanded configuration for deployment within an annulus of the native heart valve site.

As previously described, the heart valve prosthesis 100 includes the prosthetic valve 106 within the interior of the valve frame 104. In an embodiment hereof, the prosthetic valve 106 is positioned adjacent to an inflow end 105 of the valve frame 104. The prosthetic valve 106 is configured as a one-way valve to allow blood flow in one direction and thereby regulate blood flow therethrough. The prosthetic valve 106 is capable of blocking flow in one direction to regulate flow therethrough via valve leaflets that may form a bicuspid or tricuspid replacement valve. More particularly, if the heart valve prosthesis 100 is configured for placement within a native heart valve having two leaflets, such as the mitral valve, the prosthetic valve 106 includes two valve leaflets to form a bicuspid replacement valve that closes with pressure on the outflow and opens with pressure on the inflow. In other embodiments in accordance herewith, the prosthetic valve 106 may be a tricuspid replacement valve or may be a single leaflet replacement valve. The valve leaflets of the prosthetic valve 106 may be made of natural pericardial material obtained from, for example, heart valves, aortic roots, aortic walls, aortic leaflets, pericardial tissue, bypass grafts, blood vessels, intestinal submucosal tissue, umbilical tissue and the like from humans or animals, such as tissue from bovine, equine or porcine origins. Alternatively, the valve leaflets may be made of synthetic materials suitable for use as heart valve prosthesis leaflets in embodiments hereof including, but not limited to polyester, polyurethane, cloth materials, nylon blends, and polymeric materials. The valve leaflets are sutured or otherwise securely and sealingly attached to an inner circumference of the valve frame 104 and/or a graft material 112 which encloses or lines the valve frame 104.

The heart valve prosthesis 100 also includes one or more layers of the graft material 112. The graft material 112 is coupled to the anchoring frame 102 and/or to the valve frame 104 to prevent paravalvular leaks between the heart valve prosthesis 100 and the native tissue and/or between the anchoring frame 102 and the valve frame 104. The graft material 112 is formed from a suitable natural or biological graft material such as pericardium or another membranous tissue including, but not limited to intestinal submucosa. Alternatively, the graft material 112 may be a low-porosity woven fabric, such as polyester, polyethylene terephthalate (PET), or polytetrafluoroethylene (PTFE), which creates a one-way fluid passage when attached to the frame. In one embodiment, the graft material 112 may be a knit or woven polyester, such as a polyester or PTFE knit, which can be utilized when it is desired to provide a medium for tissue ingrowth and the ability for the fabric to stretch to conform to a curved surface. Polyester velour fabrics may alternatively be used, such as when it is desired to provide a medium for tissue ingrowth on one side and a smooth surface on the other side. In the embodiment of FIGS. 1A-1C, the heart valve prosthesis 100 includes two layers of the graft material 112. More precisely, a first layer 112A is coupled to the anchoring frame 102 and extends around an inner wall or surface of the anchoring frame 102 while a second layer 112B is coupled to the valve frame 104 and extends around an inner wall or surface of the valve frame 104. However, this is by way of example and not limitation. In other embodiments, the prosthesis 100 can have a greater or lesser number of layers of graft material. For example, the graft material 112 may be coupled to an inner and/or an outer surface of either the anchoring frame 102 and/or the valve frame 104 in any combination.

Figure 2:
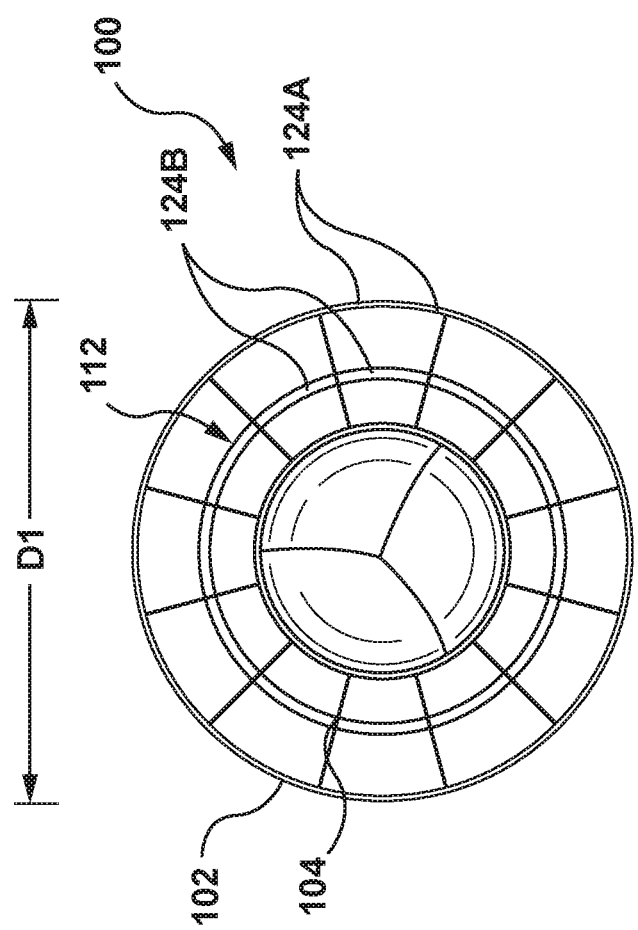
FIG. 2 depicts a cross-sectional view of the heart valve prosthesis in a radially compressed configuration, taken at line 2-2 of FIG. 1B.

The heart valve prosthesis 100 is compressed and loaded into a capsule of a delivery catheter for percutaneous delivery to a desired treatment location. The heart valve prosthesis 100 is designed to be compressed uniformly to a radially compressed configuration, as shown in FIG. 2. In the radially compressed configuration, the structural elements of the heart valve prosthesis 100, specifically the struts 124A of the anchoring frame 102 and the struts 124B of the valve frame 104, collectively referred to herein as the struts 124, are each spaced evenly about a circular perimeter, with the struts 124A of the anchoring member 102 disposed on an outer perimeter and the struts 124B of the valve frame 104 disposed on a concentric perimeter inward of the anchoring member 102. The thickness of the struts 124A and 124B and the corresponding layers of graft material 112A and 112B attached thereto limit the heart valve prosthesis 100 to a first diameter D1 when the heart valve prosthesis 100 is in the radially compressed configuration.

Figure 3:
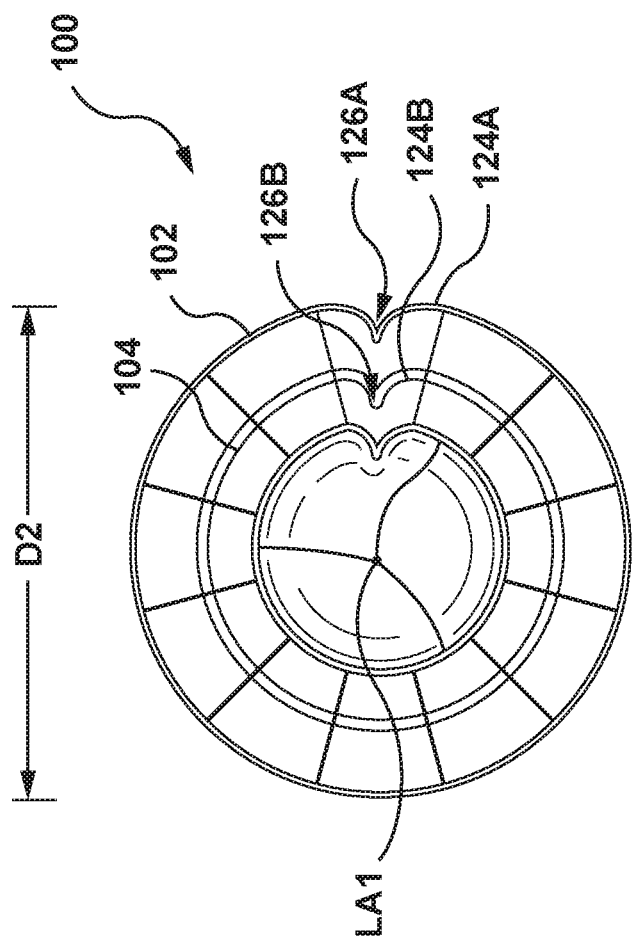
FIG. 3 depicts a cross-sectional view of the heart valve prosthesis in the radially compressed configuration, wherein a portion of the heart valve prosthesis has buckled radially inward, taken at line 3-3 of FIG. 1B.

However, at times, as the heart valve prosthesis 100 is radially compressed, a portion 126A of the anchoring frame 102 and a corresponding portion 126B of the valve frame 104 can no longer find space around their respective perimeters and may buckle inward as shown in FIG. 3. With each portion 126A, 126B buckled radially inward, the heart valve prosthesis 100 has a non-circular shape and is compressed to a second diameter D2, as shown in FIG. 3, which is smaller than the first diameter D1 of FIG. 2 described above. However, the buckling of portions 126A, 126B results in higher stress and strain being imparted on the struts 124 in and around the buckled portions. These higher stresses and strains can negatively affect the structural integrity of the anchoring frame 102 and the valve frame 104 leading to serious post-deployment complications including, but not limited to structural failure or migration of the heart valve prosthesis 100.

Figure 4:
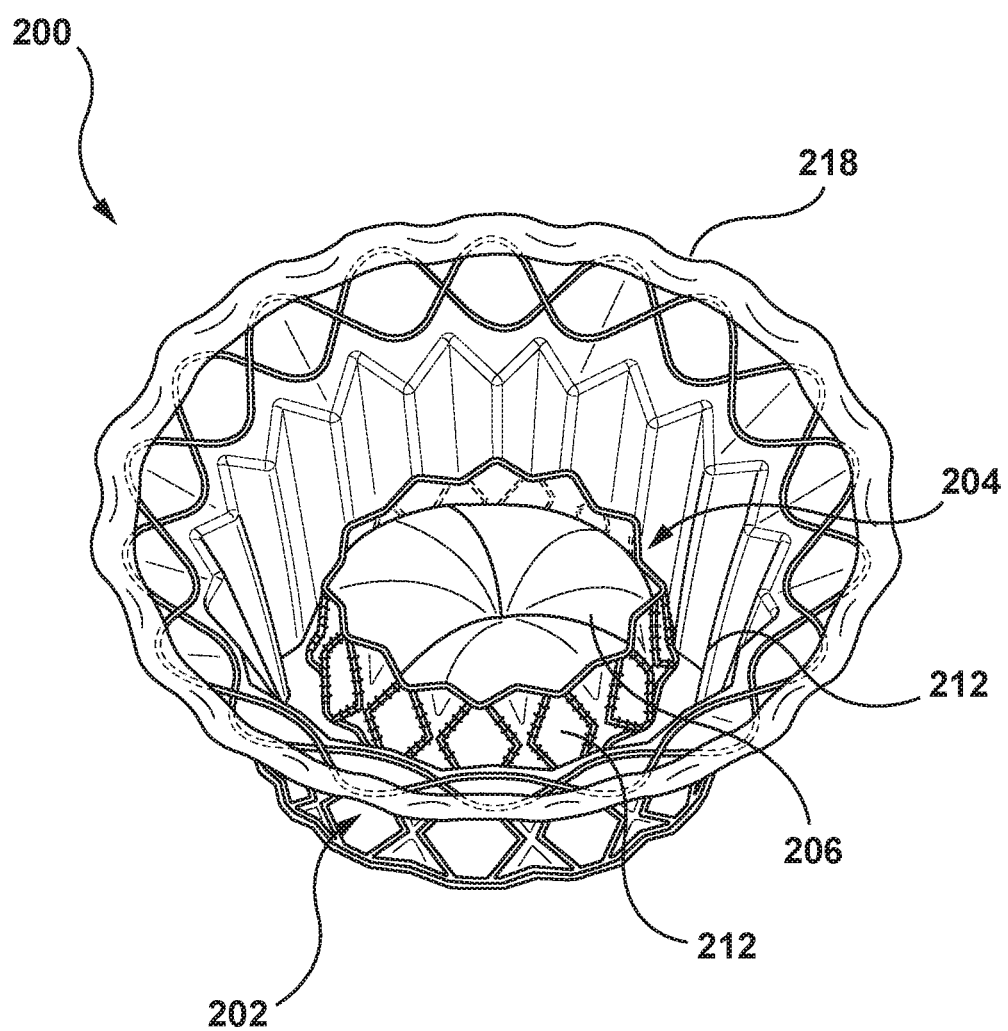
FIG. 4 depicts a perspective view of a heart valve prosthesis with a pleated configuration of longitudinal segments thereof in accordance with an embodiment hereof, wherein the heart valve prosthesis is in a radially expanded configuration.

FIG. 4 illustrates a heart valve prosthesis 200 according to an embodiment hereof in which the heart valve prosthesis 200 has pleats (i.e., infolds and outfolds) formed into the structure to result in a smaller pack-down diameter with a controlled distribution of stresses and strains. The heart valve prosthesis 200 includes an anchoring frame 202, a valve frame 204, a valve component 206, a brim 218, and a graft material 212. The valve component 206, the brim 218, and the graft material 212 are similar to the valve component 106, the brim 118, and the graft material 112 described previously. Therefore, details of these similar components will not be repeated. However, the anchoring frame 202 and the valve frame 204 of the heart valve prosthesis 200 are similar to the anchoring frame 102 and the valve frame 104 of the heart valve prosthesis 100 except that each include a plurality of outfolding longitudinal segments 232A, 232B, respectively, and collectively referred to herein as outfolding longitudinal segments 232, and a plurality of infolding longitudinal segments 234A, 234B, respectively, and collectively referred to herein as infolding longitudinal segments 234. The plurality of outfolding longitudinal segments 232 and the plurality of infolding longitudinal segments 234 are best shown in FIG. 6A, which illustrates a cross-section of the heart valve prosthesis 200 in a radially expanded configuration with the valve component 206, the graft material 212 and the brim 218 removed for clarity. As will be explained in more detail herein, the plurality of the outfolding and infolding longitudinal segments 232, 234 are configured to radially fold in opposing directions when the prosthesis 200 is in a radially compressed configuration.

Figure 5A:
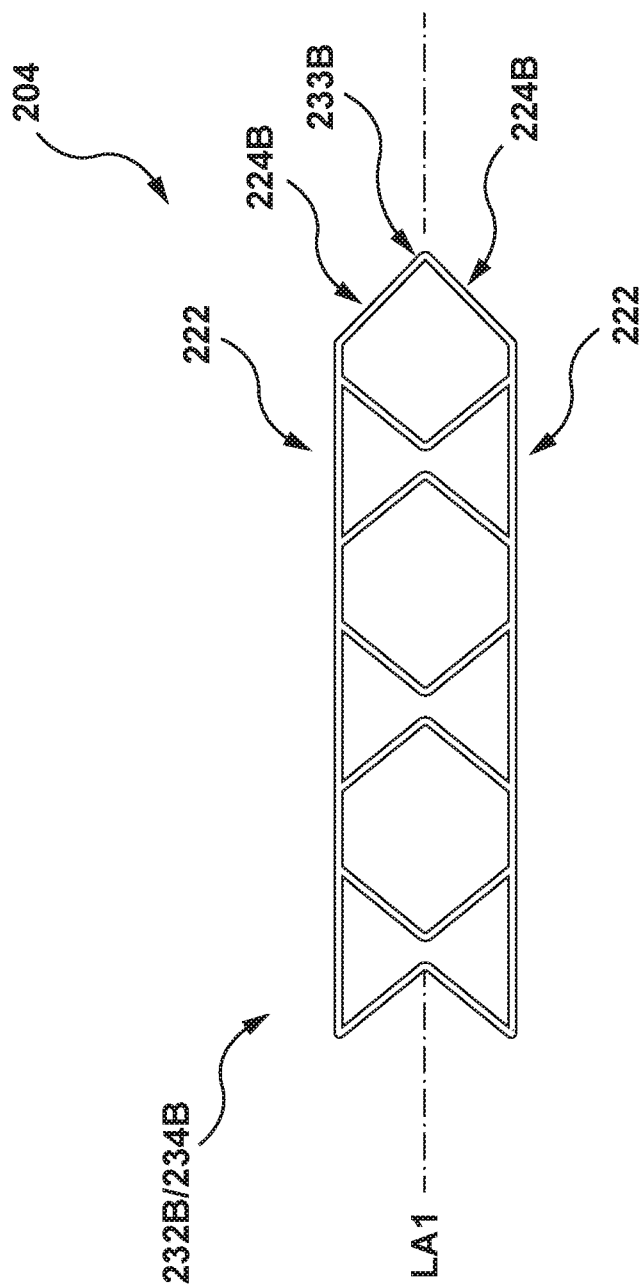
FIG. 5A depicts a side view of a longitudinal segment of a valve frame of the heart valve prosthesis of FIG. 4.

"Longitudinal segment" as used herein means an integral segment or portion of a frame, extending generally in an axial direction and parallel to the longitudinal axis LA1 of the frame for a full or entire length of the frame and extending in a circumferential direction for only a portion of the frame. For example, a longitudinal segment of the valve frame 204 is shown in FIG. 5A. The longitudinal segment shown in FIG. 5A may be configured as an outfolding longitudinal segment 232B or an infolding longitudinal segment 234B. The valve frame 204 has a similar configuration to the valve frame 104 with a plurality of posts 222 connected circumferentially by a plurality of struts 224B. The longitudinal segment of the valve frame 204 includes two circumferentially adjacent posts 222 extending the full length of the valve frame 204 and the plurality of struts 224B extending between the two circumferentially adjacent posts

222. More particularly, a pair of struts 224B extending between the two circumferentially adjacent posts 222 collectively have a V-shape and include a node or apex 233B formed therebetween. The nodes or apices 233B extending between the two circumferentially adjacent posts 222 are longitudinally or axially aligned and are herein referred to as a series of longitudinally aligned apices 233B. Thus, each outfolding longitudinal segment 232B and each infolding longitudinal segment 234B of the valve frame 204 includes a series of longitudinally aligned apices 233B.

A longitudinal segment of the anchoring frame 202 is shown in FIG. 5B. The longitudinal segment shown in FIG. 5B may be configured as an outfolding longitudinal segment 232A or an infolding longitudinal segment 234A. The anchoring frame 202 has a similar configuration to the anchoring frame 102 with a tubular scaffold of interconnected struts 224A that form the diamond-shaped openings 216. The longitudinal segment of the anchoring frame 202 includes a plurality of struts 224A that form a series of longitudinally or axially aligned diamond shaped openings 216. More particularly, each diamond shaped opening 216 of the longitudinal segment is formed by two pairs of struts 224A that collectively form one of the diamond shaped openings. Each pair of struts 224A collectively have a V-shape and include a node or apex 233A formed therebetween. The nodes or apices 233A of the longitudinal segment 226A are longitudinally or axially aligned and are herein referred to as a series of longitudinally aligned apices 233A. Thus, each outfolding longitudinal segment 232A and each infolding longitudinal segment 234A of the anchoring frame 202 includes a series of longitudinally aligned apices 233A.

As previously stated, the plurality of the outfolding and infolding longitudinal segments 232, 234 are configured to radially fold in opposing directions in a pleated configuration when the prosthesis 200 is in a radially compressed configuration. Each outfolding longitudinal segment 232A of the anchoring frame 202 has a corresponding or radially aligned outfolding longitudinal segment 232B of the valve frame 204. Similarly, each infolding longitudinal segment 234A of the anchoring frame 202 has a corresponding or radially aligned infolding longitudinal segment 234B of the valve frame 204. When the heart valve prosthesis 200 is in a radially compressed configuration as shown in FIG. 6B, each outfolding longitudinal segment 232A of the anchoring frame 202 and corresponding outfolding longitudinal segment 232B of the valve frame 204 folds radially outward such that the series of longitudinally aligned apices of each outfolding longitudinal segment are disposed radially outward from the remainder of the heart valve prosthesis 200. Further, each infolding longitudinal segment 234A of the anchoring frame 202 and corresponding infolding longitudinal segment 234B of the valve frame 204 folds radially inward such that the series of longitudinally aligned apices of each infolding longitudinal segment are disposed radially inward from the remainder of the heart valve prosthesis 200. Thus, the plurality of outfolding longitudinal segments 232 and the plurality of infolding longitudinal segments 234 create alternating folds or pleats to reduce the profile of the heart valve prosthesis 200 when the heart valve prosthesis 200 is in the radially compressed configuration.

In the pleated configuration of FIGS. 6A and 6B, the plurality of struts 224A of each longitudinal segment of the anchoring frame 202 are of an equivalent length and the plurality of struts 224B of each longitudinal segment of the valve frame 204 are of an equivalent length. Further, the infolding and outfolding longitudinal segments 234, 232 are disposed about the circumference of the respective anchoring frame 204 and the valve frame 202 in an alternating pattern, with each infolding longitudinal segment 234 being sandwiched or disposed between two adjacent outfolding longitudinal segments 232. The equivalent length of the struts 224A of the anchoring frame 202 and the equivalent length of the struts 224B of the valve frame 204, along with the alternating pattern of the infolding and outfolding longitudinal segments 234, 232, permit the infolding and outfolding longitudinal segments 234, 232 to fold like the pleats of a skirt when the heart valve prosthesis 200 is in the radially compressed configuration of FIG. 6B. The pleated configuration permits the heart valve prosthesis 200 to compress to the radially compressed configuration of FIG. 6B to a third diameter D3. The third diameter D3 of the heart valve prosthesis 200 with the plurality of infolding and outfolding longitudinal segments 234, 232 in the pleated configuration is smaller than the first diameter D1 of the heart valve prosthesis 100 of FIG. 2. Thus, the heart valve prosthesis 200 with the plurality of infolding and outfolding longitudinal segments 234, 232 folded in the pleated configuration can be compressed to a smaller profile than a similar heart valve prosthesis without the plurality of infolding and outfolding longitudinal segments folded in the pleated configuration.

When the heart valve prosthesis 200 radially expands in situ to its deployed configuration as shown in FIG. 6A, the heart valve prosthesis 200 has a generally circular perimeter or profile although the series of longitudinally aligned apices of each outfolding longitudinal segment are still disposed radially outward from the remainder of the heart valve prosthesis 200 and the series of longitudinally aligned apices of each infolding longitudinal segment are still disposed radially inward from the remainder of the heart valve prosthesis 200.

Figure 7:
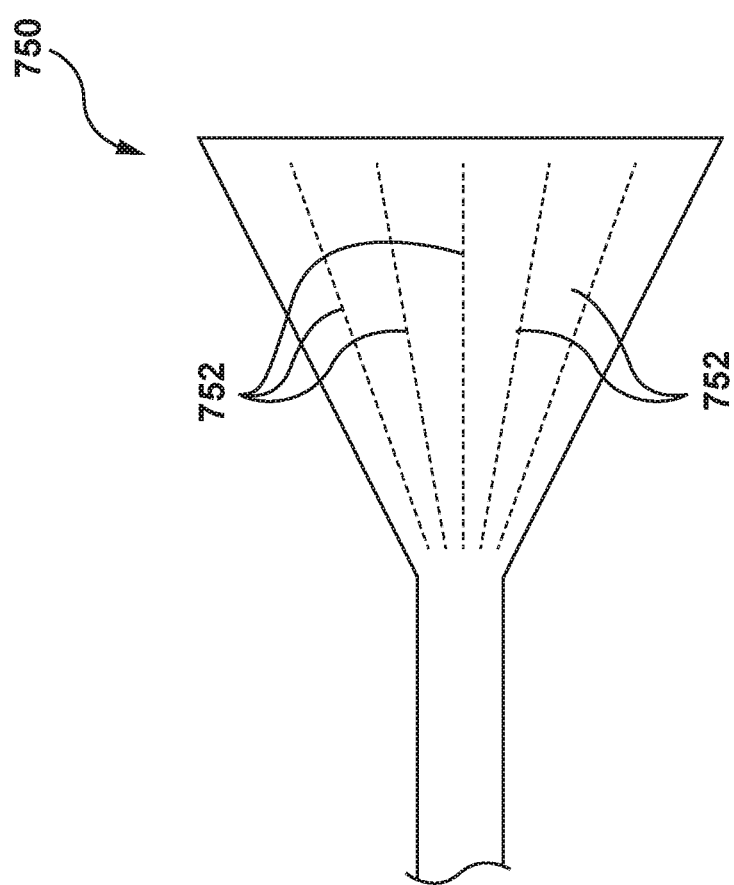
FIG. 7 depicts a side view of an exemplary loading funnel for use with embodiments hereof.

In an embodiment hereof, each outfolding and infolding longitudinal segment 232, 234 is formed by a shape-setting process. More specifically, during the shape setting process of each respective frame, the series of longitudinally aligned apices of each longitudinal segment are configured to deform or deflect radially outward or radially inward to form the outfolding or infolding longitudinal segment, respectively. Further, although not required, the deformation or folding of each infolding longitudinal segment 234 may be aided by additional tools or fixtures such as but not limited to a loading cone or funnel 750 having a plurality of longitudinal ribs 752 as shown in FIG. 7. The loading funnel 750 can be of a variety of shapes and sizes of an infundibular cone, or a truncated cone, such as a frustum. The longitudinal ribs 752 of the loading funnel 750 are radially spaced around an inner surface of the loading funnel 750 and may extend for a portion or the entire length of the loading funnel 750. Each longitudinal rib 752 of the loading funnel 750 corresponds in placement to one of the infolding longitudinal segments 234 of the heart valve prosthesis 200. Each longitudinal rib 752 of the loading funnel 750 is configured to assist in folding the corresponding infolding longitudinal segment 234 radially inward as the heart valve prosthesis 200 is drawn through the loading funnel 750 and loaded in the radially compressed configuration within a delivery catheter. More precisely, as the heart valve prosthesis 200 is drawn into the loading funnel 750, each longitudinal rib 752 exerts a radially inward pressure onto the heart valve prosthesis 200 along the corresponding infolding longitudinal segment 234 to assist the corresponding infolding longitudinal segment 234 to fold or deform radially inward.

Figure 10B:
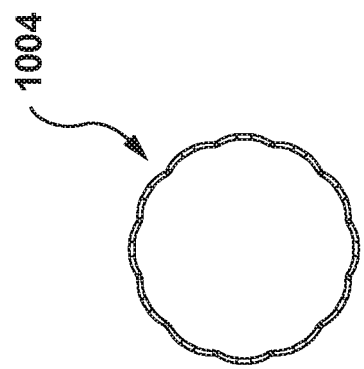
FIG. 10B depicts an end view of the valve frame of FIG. 10A.
Figure 10A:
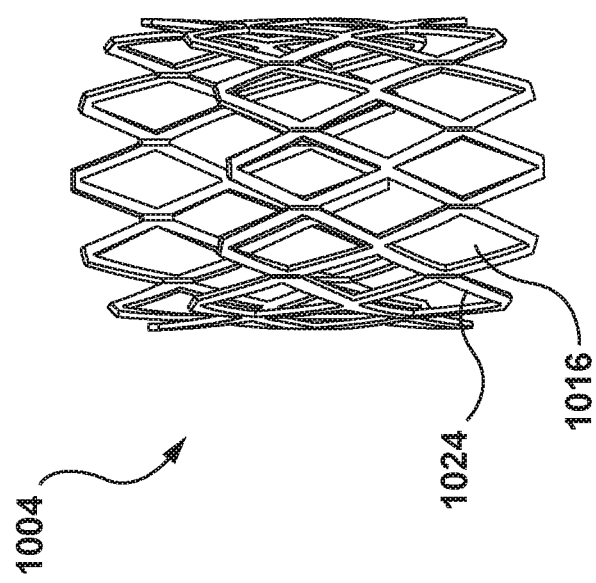
FIG. 10A depicts a perspective view of an exemplary heart valve prosthesis for use in embodiments hereof, wherein the heart valve prosthesis is in a radially expanded configuration.

In another embodiment hereof, embodiments hereof may be formed by a laser cutting processes in which the frame is laser cut from a custom cross-section tube. More particularly, a frame 1004 is shown in FIGS. 10A and 10B, which are perspective and end views of the frame 1004. More particularly, a metal tube has a custom cross-section of the end view of the frame 1004. The metal tube is laser cut into the desired geometry, creating a tubular scaffold of interconnected struts 1024 that form the diamond-shaped openings 1016. Since the custom cross-section of the metal tube has a pleat-like or flower configuration, no shape setting processes or additional tools are required for forming the pleat-like or flower configuration thereof.

In another embodiment, rather than a pleated configuration, a heart prosthesis may include a plurality of outfolding and infolding longitudinal segments that are formed in a lobed or focal area configuration. More particularly, as shown in FIGS. 8A and 8B, a heart prosthesis 200' is shown that includes an anchoring frame 202' and a valve frame 204'. The anchoring frame 202' and the valve frame 204' of the heart valve prosthesis 200' each include a plurality of outfolding longitudinal segments 232A', 232B', respectively, and collectively referred to herein as outfolding longitudinal segments 232', and a plurality of infolding longitudinal segments 234A', 234B', respectively, and collectively referred to herein as infolding longitudinal segments 234'. The plurality of outfolding longitudinal segments 232' and the plurality of infolding longitudinal segments 234' are best shown in FIG. 8A, which illustrates a cross-section of the heart valve prosthesis 200' in a radially expanded configuration. Each outfolding longitudinal segment 232A' of the anchoring frame 202' has a corresponding or radially aligned outfolding longitudinal segment 232B' of the valve frame 204'. Similarly, each infolding longitudinal segment 234A' of the anchoring frame 202' has a corresponding or radially aligned infolding longitudinal segment 234B' of the valve frame 204'.

In the lobed configuration, the infolding and outfolding longitudinal segments 234', 232' do not have an alternating pattern as in the pleated configuration of FIGS. 6A and 6B. Rather, in the embodiment of FIGS. 8A and 8B, there are a total of three (3) infolding longitudinal segments 234', with infolding longitudinal segments 234' being separated circumferentially by three (3) outfolding longitudinal segments 232'. The three (3) infolding longitudinal segments 234' create three (3) deformation focal areas 235' and permit the infolding longitudinal segments 234' to deform into the lobed or focal area configuration of FIG. 8B when the heart valve prosthesis 200' is in the radially compressed configuration. More specifically, as the heart valve prosthesis 200' is compressed radially as shown on FIG. 8B, each outfolding longitudinal segment 232' bows radially outward and each infolding longitudinal segment 234' folds or deforms radially inward. Each infolding longitudinal segment 234A' of the anchoring frame 202' and corresponding infolding longitudinal segment 234B' of the valve frame 204' folds radially inward such that the series of longitudinally aligned apices of each infolding longitudinal segment are disposed radially inward from the remainder of the heart valve prosthesis 200'. The deformation focal areas 235' permit the heart valve prosthesis 200' to be compressed to a radially compressed configuration with a fourth diameter D4, as shown in FIG. 8B. The fourth diameter D4 of the heart valve prosthesis 200' is smaller than the first diameter D1 of the heart valve prosthesis 100 of FIG. 2. Accordingly, the heart valve prosthesis 200' with the plurality of infolding and outfolding longitudinal segments 234', 232' formed in the lobed or focal area configuration can be compressed to a smaller profile than a similar heart valve prosthesis without the plurality of infolding and outfolding longitudinal segments formed in the lobed or focal area configuration.

When the heart valve prosthesis 200' radially expands in situ to its deployed configuration as shown in FIG. 8A, the heart valve prosthesis 200' has a generally circular perimeter or profile although the deformation focal areas 235' are still disposed radially inward from the remainder of the heart valve prosthesis 200.

While the embodiment of heart valve prosthesis 200' has been described with each pair of infolding longitudinal segments 234' being separated circumferentially by three (3) outfolding longitudinal segments 232', this is by way of example and not limitation. It will be understood that more or fewer outfolding longitudinal segments 232' may separate each pair of infolding longitudinal segments 234'. Further, while shown in FIGS. 8A and 8B with three (3) infolding longitudinal segments 234' creating a total of three deformation focal areas 235', this too is by way of example and not limitation, and more or fewer infolding longitudinal segments 234' may be utilized with the lobed configuration.

Figure 9B:
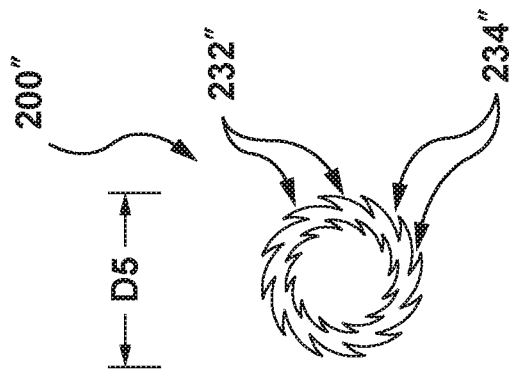
FIG. 9B depicts cross-sectional view of the heart valve prosthesis of FIG. 9A, wherein the heart valve prosthesis is in a radially compressed configuration.
Figure 9A:
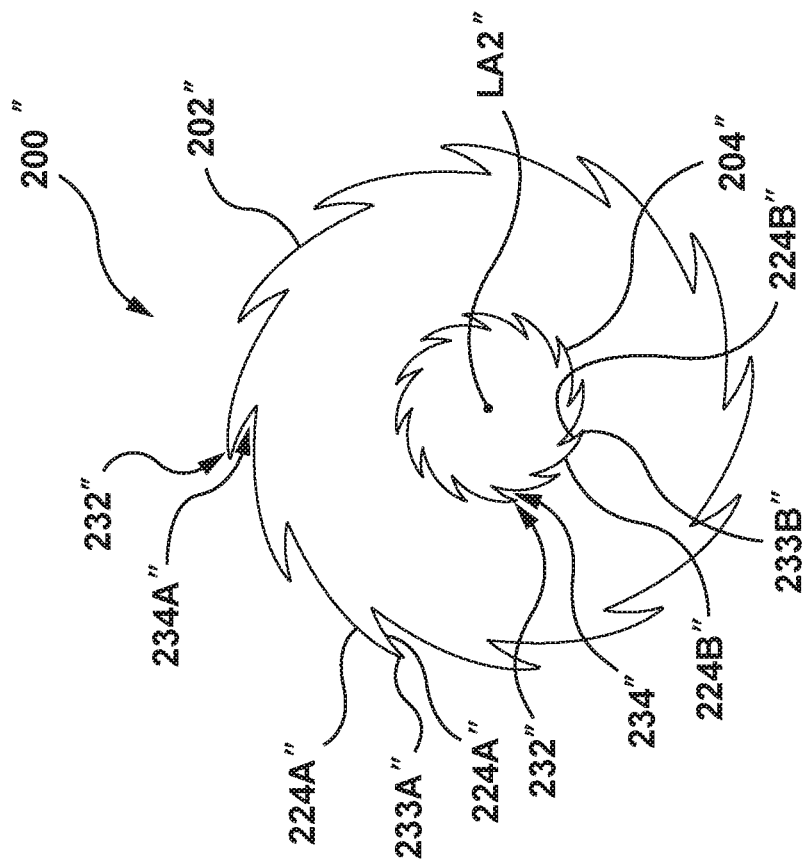
FIG. 9A depicts a cross-sectional view of a heart valve prosthesis with a spiral configuration of longitudinal segments thereof in accordance with and embodiment hereof, wherein the heart valve prosthesis is in a radially expanded configuration.

In yet another embodiment, rather than a pleated or lobed configuration, a heart prosthesis may include a plurality of outfolding and infolding longitudinal segments that are formed in a sawtooth or spiral configuration. More particularly, as shown in FIGS. 9A and 9B, a heart prosthesis 200" is shown that includes an anchoring frame 202" and a valve frame 204". The anchoring frame 202" and the valve frame 204" of the heart valve prosthesis 200" each include a plurality of outfolding longitudinal segments 232A", 232B", respectively, and collectively referred to herein as outfolding longitudinal segments 232", and a plurality of infolding longitudinal segments 234A", 234B", respectively, and collectively referred to herein as infolding longitudinal segments 234". The plurality of outfolding longitudinal segments 232" and the plurality of infolding longitudinal segments 234" are best shown in FIG. 9A, which illustrates a cross-section of the heart valve prosthesis 200" in a radially expanded configuration. Each outfolding longitudinal segment 232A" of the anchoring frame 202" has a corresponding or radially aligned outfolding longitudinal segment 232B" of the valve frame 204". Similarly, each infolding longitudinal segment 234A" of the anchoring frame 202" has a corresponding or radially aligned infolding longitudinal segment 234B" of the valve frame 204".

In the sawtooth or spiral configuration, the infolding and outfolding longitudinal segments 234", 232" have an alternating pattern that fold in opposing directions similar to the pleated configuration of FIGS. 6A and 6B. However, in the sawtooth or spiral configuration the plurality of outfolding longitudinal segments 232" and the plurality of infolding longitudinal segments 234" fold in a circumferentially overlapping manner. More particularly, when the heart valve prosthesis 200" is in a radially compressed configuration as shown in FIG. 9B, each outfolding longitudinal segment 232A" of the anchoring frame 202" and corresponding outfolding longitudinal segment 232B" of the valve frame 204" folds radially outward such that the series of longitudinally aligned apices of each outfolding longitudinal segment are disposed radially outward from the remainder of the heart valve prosthesis 200". Further, each infolding longitudinal segment 234A" of the anchoring frame 202" and corresponding infolding longitudinal segment 234B" of the valve frame 204" folds radially inward such that the series of longitudinally aligned apices of each infolding longitudinal segment are disposed radially inward from the remainder of the heart valve prosthesis 200". However, unlike the pleated configuration in which the struts thereof are of an equivalent length, adjacent struts 224A" of a longitudinal segment of the anchoring frame 204" (forming an apex 233A" therebetween) are of dissimilar lengths, and adjacent struts 224B" of a longitudinal segment of the valve frame 202" (forming an apex 233B" therebetween) are of dissimilar length. The dissimilar lengths of the struts create a series of circumferentially overlapping folds spiraling about the longitudinal axis LA2" of the heart valve prosthesis 200". This permits the heart valve prosthesis 200" to be compressed to a fifth diameter D5 when in the radially compressed configuration, as shown in FIG. 9B. The fifth diameter D5 of the heart valve prosthesis 200" with the plurality of outfolding longitudinal segments 232" and the plurality of infolding longitudinal segments 234" in the spiral configuration is smaller than the first diameter D1 of FIG. 2 of the heart valve prosthesis 100. Thus, the heart valve prosthesis 200" with the plurality of infolding and outfolding longitudinal segments 234", 232" folded in the spiral configuration can be compressed to a smaller profile than a similar heart valve prosthesis without the plurality of infolding and outfolding longitudinal segments folded in the spiral.

When the heart valve prosthesis 200" radially expands in situ to its deployed configuration as shown in FIG. 9A, the heart valve prosthesis 200" has a generally circular perimeter or profile although the series of longitudinally aligned apices of each outfolding longitudinal segment are still disposed radially outward from the remainder of the heart valve prosthesis 200" and the series of longitudinally aligned apices of each infolding longitudinal segment are still disposed radially inward from the remainder of the heart valve prosthesis 200".

While a specific number of outfolding longitudinal segments 232, 232', or 232" and/or infolding longitudinal segments 234, 234', or 234" are shown in each of the FIGS. 4-9B, this is not meant to be limiting, and more or fewer outfolding longitudinal segments 232, 232', 232" and/or infolding longitudinal segments 234, 234', or 234" may be utilized. Moreover, although the embodiments of FIGS. 4-9B have been described with either a pleated, lobed, or sawtooth configuration, it will be understood that other configurations are possible. Additionally, while the heart valve prostheses 200, 200', and 200" each appears to be of a shape other than circular when viewed in cross-section, it will be understood that the illustrations are magnified, and the heart valve prostheses 200, 200', and 200" each retain a generally circular perimeter in both the radially expanded state and the radially compressed state.

Further, although pleated, lobed, or sawtooth configurations are illustrated in FIGS. 4-9B with a heart valve prosthesis having dual frames, i.e., an anchoring frame and a valve frame disposed concentrically within the anchoring frame, it will be understood by one of ordinary skill in the art that a valve prosthesis having only a single frame may have a pleated, lobed, or sawtooth configuration as described herein. In addition, although embodiments described above include both infolding and outfolding longitudinal segments, in another embodiment hereof a heart valve prosthesis is configured to have only a plurality of infolding longitudinal segments. Such an example will be described in more detail with respect to FIGS. 11A-13C.

Figure 11A:
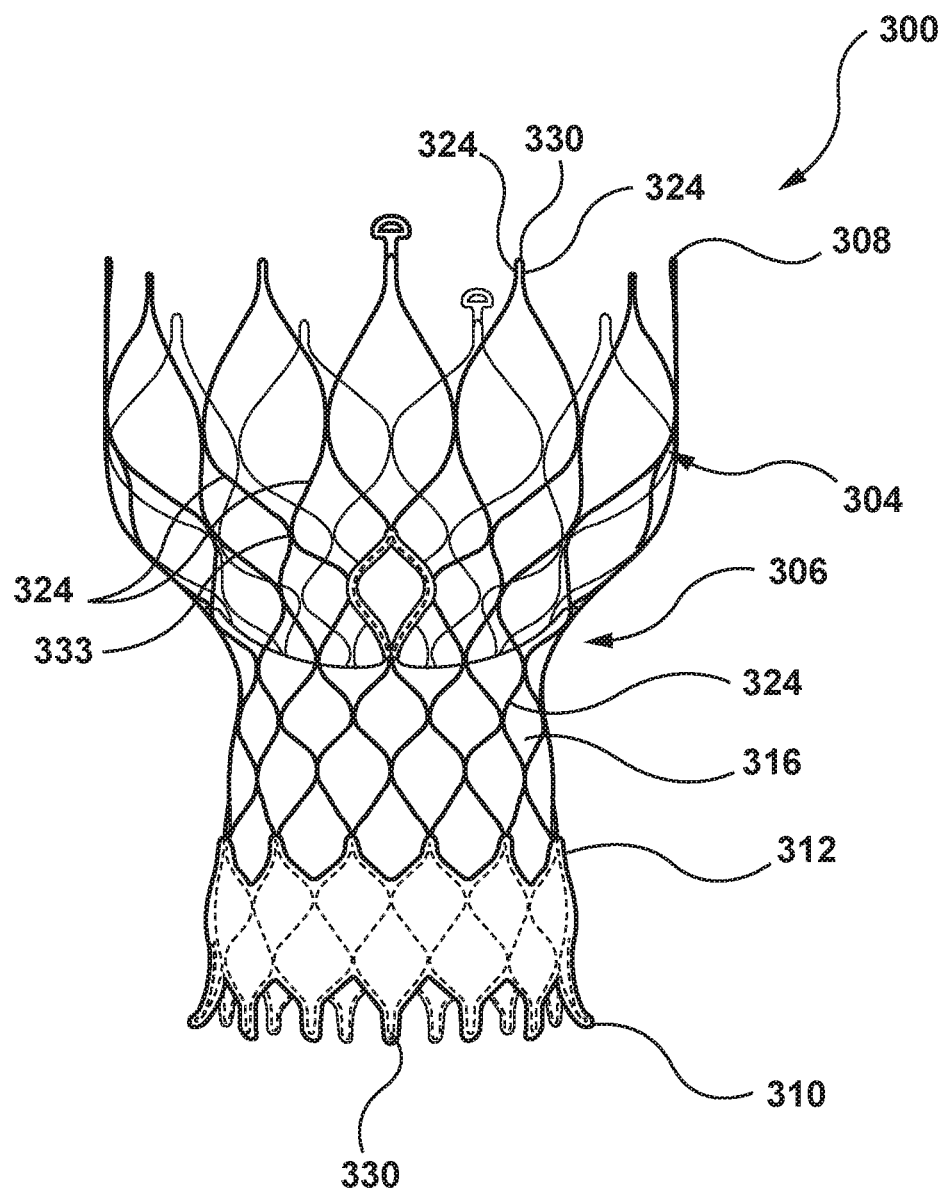
FIG. 11A depicts a perspective view of an exemplary heart valve prosthesis for use in embodiments hereof, wherein the heart valve prosthesis is in a radially expanded configuration.
Figure 11B:
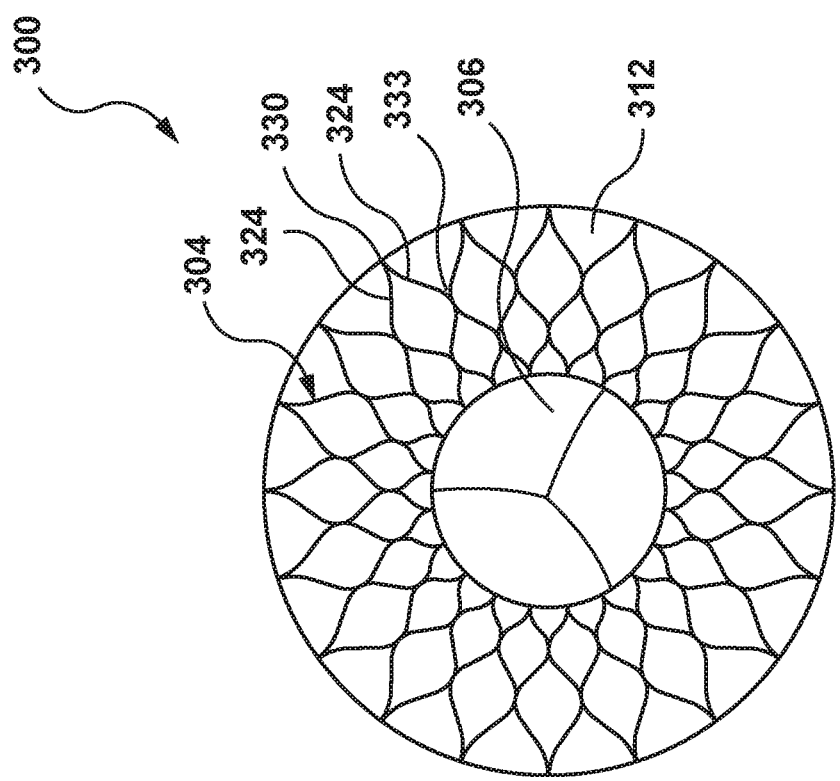
FIG. 11B depicts a cross-sectional view of the heart valve prosthesis of FIG. 11A, wherein the heart valve prosthesis is in the radially expanded configuration.
Figure 12:
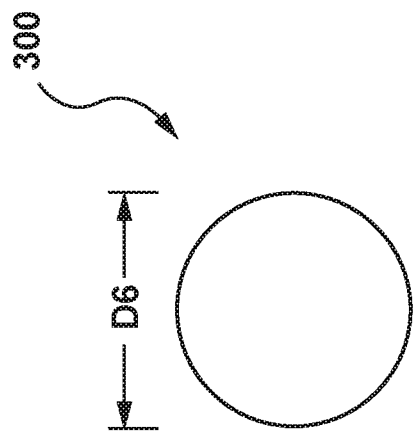
FIG. 12 depicts a cross-sectional view of the heart valve prosthesis of FIG. 11A, wherein the heart valve prosthesis is in a radially compressed configuration.

FIGS. 11A-11B are perspective and top views, respectively, of an exemplary heart valve prosthesis 300 for use in embodiments hereof. The heart valve prosthesis 300 is shown in a radially expanded configuration. The heart valve prosthesis 300 is merely exemplary and is similar to heart valve prostheses described in more detail in U.S. Pat. No. 8,226,710 to Nguyen et al., previously incorporated by reference herein in its entirety. The heart valve prosthesis 300 includes a frame 304, a graft material 312 similar to the graft material 112 described previously, and a valve component 306 similar to the valve component 106 described previously. In embodiments hereof, the frame 304 is self-expanding to return to a radially expanded configuration from a radially compressed configuration. The frame 304 is a generally tubular frame or stent, including an inflow portion 310 and an outflow portion 308 opposite the upstream end 310. When configured as a replacement for an aortic valve, the upstream end 310 of the heart valve prosthesis 300 extends into and anchors within the aortic annulus of a patient's left ventricle and the downstream end 308 is positioned in the patient's ascending aorta. The frame 304 is a tubular scaffold of interconnected struts 324 that form diamond-shaped openings 316. Adjacent struts 324 come together to form nodes or apices 333. Each node or apex disposed at the upstream or downstream ends 310, 308 is known as a crown 330. The heart valve prosthesis 300 has a sixth diameter D6 when the heart valve prosthesis 300 is in the radially compressed configuration, as shown in FIG. 12.

FIGS. 13A and 13B illustrate a heart valve prosthesis 400 according to another embodiment hereof which is configured to have only a plurality of infolding longitudinal segments. Heart valve prosthesis 400 is similar to heart valve prosthesis 300 described above, except that a frame 404 thereof includes a plurality of infolding longitudinal segments 434. The infolding longitudinal segments 434 are similar to the infolding longitudinal segments 234 previously described with respect to FIG. 4. Each infolding longitudinal segment 434 includes a plurality of struts 424 that form a series of longitudinally or axially aligned diamond shaped openings as best shown in FIG. 13C. More particularly, each diamond shaped opening 416 of the infolding longitudinal segment 434 is formed by two pairs of struts 424 that collectively form one of the diamond shaped openings. Each pair of struts 424 collectively have a V-shape and include a node or apex 433 formed therebetween. Each node or apex disposed at the upstream or downstream ends of the infolding longitudinal segment is known as a crown 430. The nodes or apices 433 of the infolding longitudinal segment 434 (including the crowns 430 disposed at the ends thereof) are longitudinally or axially aligned and are herein referred to as a series of longitudinally aligned apices 433. Thus, each infolding longitudinal segment 434 of the frame 404 includes a series of longitudinally aligned apices 433.

In the embodiment of FIGS. 13A and 13B, the frame 404 includes four (4) infolding longitudinal segments 434, as best shown in FIG. 13A, which illustrates a cross-section of the heart valve prosthesis 400 in a radially expanded configuration. While the heart valve prosthesis 400 is shown with four (4) infolding longitudinal segments 434, this is not meant to be limiting. In other embodiments, more or fewer infolding longitudinal segments 434 may be utilized. The plurality of the infolding longitudinal segments 434 are configured to fold radially inward to an infold-only configuration when the heart valve prosthesis 400 is in a radially compressed configuration, shown in FIG. 13B. When the heart valve prosthesis 400 is in the radially compressed configuration, the series of longitudinally aligned apices 433 of each infolding longitudinal segment 434 are disposed radially inward from the remainder of the heart valve prosthesis 400.

Each infolding longitudinal segment 434 is formed as previously described with respect to the infolding longitudinal segments 234 of FIGS. 6A-6B and extends for the entire length of the heart valve prosthesis 400. Accordingly, each infolding longitudinal segment 434 is configured to fold or deform radially inward when the heart valve prosthesis 400 is in the radially compressed configuration. The radially inward folding of the infolding longitudinal segments 434 permit the heart valve prosthesis 400 to compress to the radially compressed configuration of FIG. 13B to a seventh diameter D7. The seventh diameter D7 of the heart valve prosthesis 400 in the radially compressed configuration with the plurality of infolding longitudinal segments 434 folded radially inward is smaller than the sixth diameter D6 of the heart valve prosthesis 300 in the radially compressed configuration without a plurality of infolding longitudinal segments. Thus, the heart valve prosthesis 400 with the plurality of infolding longitudinal segments 434 folded in the infold-only configuration can be compressed to a smaller profile than a similar heart valve prosthesis without the plurality of infolding longitudinal segments folded in the infold-only configuration.

When the heart valve prosthesis 400 radially expands in situ to its deployed configuration as shown in FIG. 13A, the heart valve prosthesis 400 has a generally circular perimeter or profile although the series of longitudinally aligned apices of each infolding longitudinal segment are still disposed radially inward from the remainder of the heart valve prosthesis 400.

According to a first embodiment hereof, a prosthesis has a radially expanded configuration and a radially compressed configuration. The prosthesis includes a frame with an infolding longitudinal segment. The infolding longitudinal segment of the frame extends an entire length of the frame and is configured to fold radially inward when the prosthesis is in the radially compressed configuration such that a series of longitudinally aligned apices of the infolding longitudinal segment is disposed radially inward of the remainder of the prosthesis.

In an aspect of the first embodiment, and in combination with any other aspects herein, the frame further includes an outfolding longitudinal segment. The outfolding longitudinal segment of the frame extends an entire length of the frame and is configured to fold radially outward when the prosthesis is in the radially compressed configuration such that a series of longitudinally aligned apices of the outfolding longitudinal segment is disposed radially outward of the remainder of the prosthesis.

In an aspect of the first embodiment, and in combination with any other aspects herein, frame includes a plurality of infolding longitudinal segments and a plurality of outfolding longitudinal segments.

In an aspect of the first embodiment, and in combination with any other aspects herein, the plurality of infolding longitudinal segments and the plurality of outfolding longitudinal segments alternate and fold in a pleated configuration.

In an aspect of the first embodiment, and in combination with any other aspects herein, the plurality of infolding longitudinal segments and the plurality of outfolding longitudinal segments alternate and fold in a sawtooth configuration.

In an aspect of the first embodiment, and in combination with any other aspects herein, the plurality of infolding longitudinal segments and the plurality of outfolding longitudinal segments fold in a lobed configuration.

In an aspect of the first embodiment, and in combination with any other aspects herein, the prosthesis is a heart valve prosthesis and the prosthesis further comprising a prosthetic valve component disposed within and coupled to the frame.

In an aspect of the first embodiment, and in combination with any other aspects herein, the prosthesis further includes a graft material.

In an aspect of the first embodiment, and in combination with any other aspects herein, the graft material is coupled of an inner surface of the frame.

In an aspect of the first embodiment, and in combination with any other aspects herein, the graft material is coupled to an outer surface of the frame.

According to a second embodiment hereof, a heart valve prosthesis has a radially expanded configuration and a radially compressed configuration. The heart valve prosthesis includes a valve frame including an infolding longitudinal segment. The infolding longitudinal segment of the valve frame extends an entire length of the valve frame and is configured to fold radially inward when the prosthesis is in the radially compressed configuration such that a series of longitudinally aligned apices of the infolding longitudinal segment is disposed radially inward of the remainder of the prosthesis. The heart valve prosthesis also includes an anchoring frame surrounding and coupled to the valve frame, the anchoring frame including an infolding longitudinal segment that extends an entire length of the anchoring frame and is configured to fold radially inward when the prosthesis is in the radially compressed configuration such that a series of longitudinally aligned apices of the infolding longitudinal segment is disposed radially inward of the remainder of the prosthesis. A prosthetic valve component is coupled to the valve frame, and a graft material is coupled to at least one of the valve frame and the anchoring frame. The infolding longitudinal segment of the anchoring frame is radially aligned with the infolding longitudinal segment of the valve frame.

In an aspect of the second embodiment, and in combination with any other aspects herein, the valve frame further includes an outfolding longitudinal segment that extends an entire length of the valve frame and is configured to fold radially outward when the heart valve prosthesis is in the radially compressed configuration such that a series of longitudinally aligned apices of the outfolding longitudinal segment is disposed radially outward of the remainder of the heart valve prosthesis, and the anchoring frame further includes an outfolding longitudinal segment that extends an entire length of the anchoring frame and is configured to fold radially outward when the heart valve prosthesis is in the radially compressed configuration such that a series of longitudinally aligned apices of the outfolding longitudinal segment is disposed radially outward of the remainder of the heart valve prosthesis. The outfolding longitudinal segment of the anchoring frame is radially aligned with the outfolding longitudinal segment of the valve frame.

In an aspect of the second embodiment, and in combination with any other aspects herein, the valve frame includes a plurality of infolding longitudinal segments and a plurality of outfolding longitudinal segments. The anchoring frame includes a plurality of infolding longitudinal segments and a plurality of outfolding longitudinal segments, each outfolding longitudinal segment of the anchoring frame being radially aligned with an outfolding longitudinal segment of the valve frame.

In an aspect of the second embodiment, and in combination with any other aspects herein, the plurality of infolding longitudinal segments of the valve frame and the plurality of outfolding longitudinal segments of the valve frame alternate and fold in a pleated configuration. The plurality of infolding longitudinal segments of the anchoring frame and the plurality of outfolding longitudinal segments of the anchoring frame alternate and fold in a pleated configuration.

In an aspect of the second embodiment, and in combination with any other aspects herein, the plurality of infolding longitudinal segments of the valve frame and the plurality of outfolding longitudinal segments of the valve frame alternate and fold in a sawtooth configuration. The plurality of infolding longitudinal segments of the anchoring frame and the plurality of outfolding longitudinal segments of the anchoring frame alternate and fold in a sawtooth configuration.

In an aspect of the second embodiment, and in combination with any other aspects herein, the plurality of infolding longitudinal segments of the valve frame and the plurality of outfolding longitudinal segments of the valve frame fold in a lobed configuration. The plurality of infolding longitudinal segments of the anchoring frame and the plurality of outfolding longitudinal segments of the anchoring frame fold in a lobed configuration.

In an aspect of the second embodiment, and in combination with any other aspects herein, the heart valve prosthesis is configured for placement within a mitral heart valve in situ.

In an aspect of the second embodiment, and in combination with any other aspects herein, the graft material is coupled to an inner surface of the valve frame and an inner surface of the anchoring frame.

According to a third embodiment hereof, a prosthesis has a radially expanded configuration and a radially compressed configuration. The prosthesis includes a frame including a plurality of infolding longitudinal segments and a plurality of outfolding longitudinal segments. Each of the infolding longitudinal segments of the frame extend an entire length of the frame and is configured to deform radially inward when the prosthesis is in the radially compressed configuration such that a series of longitudinally aligned apices of each infolding longitudinal segment is disposed radially inward of the remainder of the prosthesis. Each of the outfolding longitudinal segments of the frame extend an entire length of the frame and is configured to deform radially outward when the prosthesis is in the radially compressed configuration such that a series of longitudinally aligned apices of each outfolding longitudinal segment is disposed radially outward of the remainder of the prosthesis.

In an aspect of the third embodiment, and in combination with any other aspects herein, the pluralities of the infolding and outfolding longitudinal segments alternate and fold in a pleated configuration when the prosthesis is in the radially compressed configuration.

While various embodiments have been described above, it should be understood that they have been presented only as illustrations and examples of the present invention, and not by way of limitation. It will be apparent to persons skilled in the relevant art that various changes in form and detail can be made therein without departing from the spirit and scope of the invention. Thus, the breadth and scope of the present invention should not be limited by any of the above-described exemplary embodiments but should be defined only in accordance with the appended claims and their equivalents. It will also be understood that each feature of each embodiment discussed herein can be used in combination with the features of any other embodiment.

What is claimed is:

1. A prosthesis having a radially expanded configuration and a radially compressed configuration, the prosthesis comprising: an inner frame including a tubular scaffold of interconnected struts, an apex being formed between a pair of struts of the interconnected struts, wherein an infolding longitudinal segment of the tubular scaffold includes a series of longitudinally aligned apices, the infolding longitudinal segment of the inner frame extending parallel to a longitudinal axis of the inner frame, wherein when the prosthesis is in the radially compressed configuration, the infolding longitudinal segment folds radially inwards such that the series of longitudinally aligned apices of the infolding longitudinal segment is disposed radially inward of the remainder of the inner frame; and an outer frame surrounding and coupled to the inner frame, the outer frame including a tubular scaffold of interconnected struts, an apex being formed between a pair of struts of the interconnected struts, wherein an infolding longitudinal segment of the tubular scaffold includes a series of longitudinally aligned apices, the infolding longitudinal segment extending parallel to a longitudinal axis of the outer frame, wherein when the prosthesis is in the radially compressed configuration, the infolding longitudinal segment folds radially inwards such that the series of longitudinally aligned apices of the infolding longitudinal segment is disposed radially inward of the remainder of the outer frame, wherein the infolding longitudinal segment of the outer frame is radially aligned with the infolding longitudinal segment of the inner frame; and a prosthetic valve component coupled the inner frame.

2. The prosthesis of claim 1, wherein the inner frame further includes an outfolding longitudinal segment that includes a second series of longitudinally aligned apices, the outfolding longitudinal segment of the inner frame extending parallel to the longitudinal axis of the inner frame, wherein when the prosthesis is in the radially compressed configuration, the outfolding longitudinal segment folds radially outwards such that the second series of longitudinally aligned apices of the outfolding longitudinal segment is disposed radially outward of the remainder of the inner frame; wherein the outer frame further includes an outfolding longitudinal segment that includes a second series of longitudinally aligned apices, the outfolding longitudinal segment of the outer frame extending parallel to a longitudinal axis of the outer frame, wherein when the heart valve prosthesis is in the radially compressed configuration, the outfolding longitudinal segment folds radially outwards such that the second series of longitudinally aligned apices of the outfolding longitudinal segment is disposed radially outward of the remainder of the outer frame, and wherein the outfolding longitudinal segment of the outer frame is radially aligned with the outfolding longitudinal segment of the inner frame.

3. The prosthesis of claim 2, wherein the inner frame includes a plurality of infolding longitudinal segments and a plurality of outfolding longitudinal segments and wherein the outer frame includes a plurality of infolding longitudinal segments and a plurality of outfolding longitudinal segments, each outfolding longitudinal segment of the outer frame being radially aligned with an outfolding longitudinal segment of the inner frame.

4. The prosthesis of claim 3, wherein the plurality of infolding longitudinal segments of the inner frame and the plurality of outfolding longitudinal segments of the inner frame alternate and fold in a pleated configuration, and wherein the plurality of infolding longitudinal segments of the outer frame and the plurality of outfolding longitudinal segments of the outer frame alternate and fold in a pleated configuration.

5. The prosthesis of claim 3, wherein the plurality of infolding longitudinal segments of the inner frame and the plurality of outfolding longitudinal segments of the inner frame alternate and fold in a sawtooth configuration, and wherein the plurality of infolding longitudinal segments of the outer frame and the plurality of outfolding longitudinal segments of the outer frame alternate and fold in a pleated configuration.

6. The prosthesis of claim 3, wherein the plurality of infolding longitudinal segments of the inner frame and the plurality of outfolding longitudinal segments of the inner frame fold in a lobed configuration, and wherein the plurality of infolding longitudinal segments of the outer frame and the plurality of outfolding longitudinal segments of the outer frame alternate and fold in a pleated configuration.

7. The prosthesis of claim 1, further comprising a prosthetic valve component disposed within and coupled to the inner frame.

8. The prosthesis of claim 7, further comprising a graft material.

9. The prosthesis of claim 8, wherein the graft material is coupled of an inner surface of the inner frame.

10. The prosthesis of claim 8, wherein the graft material is coupled to an outer surface of the inner frame.

11. A heart valve prosthesis having a radially expanded configuration and a radially compressed configuration, the heart valve prosthesis comprising:
 a valve frame including a tubular scaffold of interconnected struts, an apex being formed between a pair of struts of the interconnected struts, wherein an infolding longitudinal segment of the tubular scaffold includes a series of longitudinally aligned apices, the infolding longitudinal segment of the valve frame extending parallel to a longitudinal axis of the valve frame, wherein when the prosthesis is in the radially compressed configuration, the infolding longitudinal segment folds radially inwards such that the series of longitudinally aligned apices of the infolding longitudinal segment is disposed radially inward of the remainder of the valve frame;
 an anchoring frame surrounding and coupled to the valve frame, the anchoring frame including a tubular scaffold of interconnected struts, an apex being formed between a pair of struts of the interconnected struts, wherein an infolding longitudinal segment of the tubular scaffold includes a series of longitudinally aligned apices, the infolding longitudinal segment extending parallel to a longitudinal axis of the anchoring frame, wherein when the prosthesis is in the radially compressed configuration, the infolding longitudinal segment folds radially inwards such that the series of longitudinally aligned apices of the infolding longitudinal segment is disposed radially inward of the remainder of the anchoring frame;
 a prosthetic valve component coupled to the valve frame; and
 a graft material coupled to at least one of the valve frame and the anchoring frame, wherein the infolding longitudinal segment of the anchoring frame is radially aligned with the infolding longitudinal segment of the valve frame.

12. The prosthesis of claim 11, wherein the valve frame further includes an outfolding longitudinal segment that includes a second series of longitudinally aligned apices, the outfolding longitudinal segment of the valve frame extending parallel to a longitudinal axis of the valve frame, wherein when the heart valve prosthesis is in the radially compressed configuration, the outfolding longitudinal segment folds radially outwards such that the second series of longitudinally aligned apices of the outfolding longitudinal segment is disposed radially outward of the remainder of the valve frame, and
 wherein the anchoring frame further includes an outfolding longitudinal segment that includes a second series of longitudinally aligned apices, the outfolding longitudinal segment of the anchoring frame extending parallel to a longitudinal axis of the anchoring frame, wherein when the heart valve prosthesis is in the radially compressed configuration, the outfolding longitudinal segment folds radially outwards such that the second series of longitudinally aligned apices of the outfolding longitudinal segment is disposed radially outward of the remainder of the anchoring frame, and
 wherein the outfolding longitudinal segment of the anchoring frame is radially aligned with the outfolding longitudinal segment of the valve frame.

13. The prosthesis of claim 12, wherein the valve frame includes a plurality of infolding longitudinal segments and a plurality of outfolding longitudinal segments and wherein the anchoring frame includes a plurality of infolding longitudinal segments and a plurality of outfolding longitudinal segments, each outfolding longitudinal segment of the anchoring frame being radially aligned with an outfolding longitudinal segment of the valve frame.

14. The prosthesis of claim 13, wherein the plurality of infolding longitudinal segments of the valve frame and the plurality of outfolding longitudinal segments of the valve frame alternate and fold in a pleated configuration, and wherein the plurality of infolding longitudinal segments of the anchoring frame and the plurality of outfolding longitudinal segments of the anchoring frame alternate and fold in a pleated configuration.

15. The prosthesis of claim 13, wherein the plurality of infolding longitudinal segments of the valve frame and the plurality of outfolding longitudinal segments of the valve frame alternate and fold in a sawtooth configuration, and wherein the plurality of infolding longitudinal segments of the anchoring frame and the plurality of outfolding longitudinal segments of the anchoring frame alternate and fold in a sawtooth configuration.

16. The prosthesis of claim 13, wherein the plurality of infolding longitudinal segments of the valve frame and the plurality of outfolding longitudinal segments of the valve frame fold in a lobed configuration, and wherein the plurality of infolding longitudinal segments of the anchoring frame and the plurality of outfolding longitudinal segments of the anchoring frame fold in a lobed configuration.

17. The heart valve prosthesis of claim 11, wherein the heart valve prosthesis is configured for placement within a mitral heart valve in situ.

18. The heart valve prosthesis of claim 11, wherein the graft material is coupled to an inner surface of the valve frame and an inner surface of the anchoring frame.

* * * * *